(12) United States Patent
Hall et al.

(10) Patent No.: US 11,622,846 B2
(45) Date of Patent: Apr. 11, 2023

(54) SUBCUTANEOUS VASCULAR ASSEMBLIES FOR IMPROVING BLOOD FLOW AND RELATED DEVICES AND METHODS

(71) Applicant: Merit Medical Systems, Inc., South Jordan, UT (US)

(72) Inventors: John William Hall, North Salt Lake, UT (US); Craig Nordhausen, Palisade, CO (US)

(73) Assignee: Merit Medical Systems, Inc., South Jordan, UT (US)

( * ) Notice: Subject to any disclaimer, the term of this patent is extended or adjusted under 35 U.S.C. 154(b) by 63 days.

(21) Appl. No.: 15/934,152

(22) Filed: Mar. 23, 2018

(65) Prior Publication Data

US 2018/0271638 A1    Sep. 27, 2018

Related U.S. Application Data

(60) Provisional application No. 62/476,124, filed on Mar. 24, 2017, provisional application No. 62/476,151, filed on Mar. 24, 2017.

(51) Int. Cl.
*A61F 2/06* (2013.01)
*A61L 27/56* (2006.01)
*A61F 2/07* (2013.01)

(52) U.S. Cl.
CPC .............. *A61F 2/06* (2013.01); *A61F 2/064* (2013.01); *A61L 27/56* (2013.01); *A61F 2/07* (2013.01); *A61F 2002/061* (2013.01); *A61F 2002/068* (2013.01)

(58) Field of Classification Search
CPC ...... A61F 2/06; A61F 2/07; A61F 2/82; A61F 2/064; A61F 2/852; A61F 2/856; A61M 16/0816; A61M 39/10; A61M 25/0014; A61M 25/00
See application file for complete search history.

(56) References Cited

U.S. PATENT DOCUMENTS

| | | | |
|---|---|---|---|
| 3,357,432 | A | 12/1967 | Sparks |
| 3,435,823 | A | 4/1969 | Edwards |
| 3,490,438 | A | 1/1970 | Lavender et al. |
| 3,683,926 | A | 8/1972 | Suzuki |
| 3,790,438 | A | 2/1974 | Lewis et al. |
| 3,814,137 | A | 6/1974 | Martinez |

(Continued)

FOREIGN PATENT DOCUMENTS

| | | |
|---|---|---|
| DE | 4418910 | 12/1995 |
| DE | 29515546 | 3/1997 |

(Continued)

OTHER PUBLICATIONS

European Search Report dated Jun. 8, 2005 for EP05006233.0.

(Continued)

*Primary Examiner* — Dinah Baria
(74) *Attorney, Agent, or Firm* — Dorsey & Whitney LLP

(57) ABSTRACT

Medical devices and related method for improving blood flow to regions of a patient are described herein. Some medical devices may include a first graft portion, a second graft portion, and a catheter portion disposed between the first graft portion and the second graft portion. The medical device may be implanted into a patient to establish a non-natural flow path.

19 Claims, 13 Drawing Sheets

(56) References Cited

U.S. PATENT DOCUMENTS

| | | | |
|---|---|---|---|
| 3,818,511 A | 6/1974 | Goldberg et al. | |
| 3,826,257 A | 7/1974 | Buselmeier | |
| 3,853,126 A | 12/1974 | Schulte | |
| 3,882,862 A | 5/1975 | Berend | |
| 3,998,222 A | 12/1976 | Shihata | |
| 4,076,023 A | 2/1978 | Martinez | |
| 4,133,312 A | 1/1979 | Burd | |
| 4,184,489 A | 1/1980 | Burd | |
| 4,214,586 A | 7/1980 | Mericle | |
| 4,318,401 A | 3/1982 | Zimmernan | |
| 4,366,819 A | 1/1983 | Kaster | |
| 4,427,219 A | 1/1984 | Madej | |
| 4,441,215 A | 4/1984 | Kaster | |
| 4,447,237 A | 5/1984 | Frisch et al. | |
| 4,496,349 A | 1/1985 | Cosentino | |
| 4,496,350 A | 1/1985 | Cosentino | |
| 4,503,568 A | 3/1985 | Madras | |
| 4,550,447 A | 11/1985 | Seiler, Jr. | |
| 4,619,641 A | 10/1986 | Schanzer | |
| 4,655,771 A | 4/1987 | Wallersten | |
| 4,723,948 A | 2/1988 | Clark et al. | |
| 4,734,094 A | 3/1988 | Jacob et al. | |
| 4,753,236 A | 6/1988 | Healy | |
| 4,771,777 A | 9/1988 | Horzewski et al. | |
| 4,772,268 A | 9/1988 | Bates | |
| 4,786,345 A | 11/1988 | Wood | |
| 4,790,826 A | 12/1988 | Elftman | |
| 4,822,341 A | 4/1989 | Colone | |
| 4,848,343 A | 7/1989 | Wallsten et al. | |
| 4,850,999 A | 7/1989 | Planck | |
| 4,856,938 A | 8/1989 | Kuehn | |
| 4,877,661 A | 10/1989 | House et al. | |
| 4,898,591 A | 2/1990 | Jang et al. | |
| 4,898,669 A | 2/1990 | Tesio | |
| 4,917,087 A | 4/1990 | Walsh et al. | |
| 4,919,127 A | 4/1990 | Pell | |
| 4,929,236 A | 5/1990 | Sampson | |
| 4,955,899 A | 9/1990 | Della Corna et al. | |
| 5,026,513 A | 6/1991 | House et al. | |
| 5,041,098 A | 8/1991 | Loiterman et al. | |
| 5,042,161 A | 8/1991 | Hodge | |
| 5,053,023 A | 10/1991 | Martin | |
| 5,061,275 A | 10/1991 | Wallsten et al. | |
| 5,061,276 A | 10/1991 | Tu et al. | |
| 5,064,435 A | 11/1991 | Porter | |
| 5,104,402 A | 4/1992 | Melbin | |
| 5,171,227 A | 12/1992 | Twardowski et al. | |
| 5,171,305 A | 12/1992 | Schickling et al. | |
| 5,192,289 A | 3/1993 | Jessen | |
| 5,192,310 A | 3/1993 | Herweck et al. | |
| 5,197,976 A | 3/1993 | Herweck et al. | |
| 5,282,860 A | 2/1994 | Matsuno et al. | |
| 5,330,500 A | 7/1994 | Song | |
| 5,336,616 A | 8/1994 | Livesey et al. | |
| 5,399,168 A | 3/1995 | Wadsworth | |
| 5,405,320 A | 4/1995 | Twardowski et al. | |
| 5,405,339 A | 4/1995 | Kohnen et al. | |
| 5,454,790 A | 10/1995 | Dubrul | |
| 5,474,268 A | 12/1995 | Yu | |
| 5,474,563 A | 12/1995 | Myler et al. | |
| 5,476,451 A | 12/1995 | Ensminger et al. | |
| 5,496,294 A | 3/1996 | Hergenrother et al. | |
| 5,509,897 A | 4/1996 | Twardowski et al. | |
| 5,558,641 A | 9/1996 | Glantz et al. | |
| 5,562,617 A | 10/1996 | Finch, Jr. et al. | |
| 5,562,618 A | 10/1996 | Cai et al. | |
| 5,591,226 A | 1/1997 | Trerotola et al. | |
| 5,607,463 A | 3/1997 | Schwartz et al. | |
| 5,624,413 A | 4/1997 | Markel et al. | |
| 5,637,088 A | 6/1997 | Wenner et al. | |
| 5,637,102 A | 6/1997 | Tolkoff et al. | |
| 5,645,532 A | 7/1997 | Horgan | |
| 5,647,855 A | 7/1997 | Trooskin | |
| 5,669,637 A | 9/1997 | Chitty et al. | |
| 5,669,881 A | 9/1997 | Dunshee | |
| 5,674,272 A | 10/1997 | Bush et al. | |
| 5,676,346 A | 10/1997 | Leinsing | |
| 5,743,894 A | 4/1998 | Swisher | |
| 5,749,880 A | 5/1998 | Banas et al. | |
| 5,755,773 A | 5/1998 | Schuster | |
| 5,755,775 A | 5/1998 | Trerotola et al. | |
| 5,755,778 A * | 5/1998 | Kleshinski | A61F 2/91 623/1.13 |
| 5,792,104 A | 8/1998 | Speckman et al. | |
| 5,797,879 A | 8/1998 | Decampli | |
| 5,800,512 A | 9/1998 | Lentz et al. | |
| 5,800,514 A | 9/1998 | Nunez et al. | |
| 5,800,522 A | 9/1998 | Campbell | |
| 5,810,870 A | 9/1998 | Myers et al. | |
| 5,830,224 A | 11/1998 | Cohn et al. | |
| 5,840,240 A | 11/1998 | Stenoien et al. | |
| 5,866,217 A | 2/1999 | Stenoien et al. | |
| 5,904,967 A | 5/1999 | Ezaki et al. | |
| 5,931,829 A | 8/1999 | Burbank et al. | |
| 5,931,865 A | 8/1999 | Silverman et al. | |
| 5,957,974 A | 9/1999 | Thompson et al. | |
| 5,997,562 A | 12/1999 | Zadno-Azizi | |
| 6,001,125 A | 12/1999 | Golds et al. | |
| 6,019,788 A | 2/2000 | Butters et al. | |
| 6,036,724 A | 3/2000 | Lentz et al. | |
| 6,102,884 A | 8/2000 | Squitieri | |
| 6,156,016 A | 12/2000 | Maginot | |
| 6,167,765 B1 | 1/2001 | Weitzel | |
| 6,171,295 B1 | 1/2001 | Garabedian | |
| 6,231,085 B1 | 5/2001 | Olson | |
| 6,245,098 B1 | 6/2001 | Feeser | |
| 6,255,396 B1 | 7/2001 | Ding et al. | |
| 6,261,255 B1 | 7/2001 | Mullis et al. | |
| 6,261,257 B1 | 7/2001 | Uflacker et al. | |
| 6,280,466 B1 | 8/2001 | Kugler et al. | |
| 6,308,992 B1 | 10/2001 | Mitsui et al. | |
| 6,309,411 B1 | 10/2001 | Lashinski et al. | |
| 6,319,279 B1 | 11/2001 | Shannon et al. | |
| 6,338,724 B1 | 1/2002 | Dossa | |
| 6,398,764 B1 | 6/2002 | Finch, Jr. et al. | |
| 6,402,767 B1 | 6/2002 | Nash et al. | |
| 6,428,571 B1 | 8/2002 | Lentz et al. | |
| 6,436,132 B1 | 8/2002 | Patel et al. | |
| 6,536,135 B2 | 3/2003 | Lipkin | |
| 6,582,409 B1 | 6/2003 | Squitieri | |
| 6,585,762 B1 | 7/2003 | Stanish | |
| 6,610,004 B2 | 8/2003 | Viole et al. | |
| 6,689,096 B1 | 2/2004 | Loubens et al. | |
| 6,689,157 B2 | 2/2004 | Madrid et al. | |
| 6,692,461 B2 | 2/2004 | Wantink | |
| 6,699,233 B2 | 3/2004 | Slanda et al. | |
| 6,702,748 B1 | 3/2004 | Nita et al. | |
| 6,702,781 B1 | 3/2004 | Reifart et al. | |
| 6,706,025 B2 | 3/2004 | Engelson et al. | |
| 6,719,781 B1 | 4/2004 | Kim | |
| 6,719,783 B2 | 4/2004 | Lentz et al. | |
| 6,730,096 B2 | 5/2004 | Basta | |
| 6,733,459 B1 | 5/2004 | Atsumi | |
| 6,740,273 B2 | 5/2004 | Lee | |
| 6,749,574 B2 | 6/2004 | O'Keefe | |
| 6,752,826 B2 | 6/2004 | Holloway et al. | |
| 6,758,836 B2 | 7/2004 | Zawacki | |
| 6,858,019 B2 | 2/2005 | McGuckin, Jr. et al. | |
| 6,926,735 B2 | 8/2005 | Henderson | |
| 6,976,952 B1 | 12/2005 | Maini et al. | |
| 6,981,987 B2 | 1/2006 | Huxel et al. | |
| 7,011,645 B2 | 3/2006 | McGuckin, Jr. et al. | |
| 7,025,741 B2 | 4/2006 | Cull | |
| 7,036,599 B2 | 5/2006 | Matteucci | |
| 7,101,356 B2 | 9/2006 | Miller | |
| 7,131,959 B2 | 11/2006 | Blatter | |
| 7,211,074 B2 | 5/2007 | Sansoucy | |
| 7,244,271 B2 | 7/2007 | Lenz et al. | |
| 7,244,272 B2 | 7/2007 | Dubson et al. | |
| 7,252,649 B2 | 8/2007 | Sherry | |
| 7,297,158 B2 | 11/2007 | Jensen | |
| 7,399,296 B2 | 7/2008 | Poole et al. | |
| 7,438,699 B2 | 10/2008 | Pecor et al. | |
| 7,452,374 B2 | 11/2008 | Hain et al. | |

(56) References Cited

U.S. PATENT DOCUMENTS

| | | |
|---|---|---|
| 7,507,229 B2 | 3/2009 | Hewitt et al. |
| 7,588,551 B2 | 9/2009 | Gertner |
| 7,708,722 B2 | 5/2010 | Glenn |
| 7,722,665 B2 | 5/2010 | Anwar et al. |
| RE41,448 E | 7/2010 | Squitieri |
| 7,753,946 B2 * | 7/2010 | Maginot ............. A61F 2/064 606/108 |
| 7,762,977 B2 | 7/2010 | Porter et al. |
| 7,789,908 B2 | 9/2010 | Sowinski et al. |
| 7,828,833 B2 | 11/2010 | Haverkost et al. |
| 7,833,214 B2 | 11/2010 | Wilson et al. |
| 7,846,139 B2 | 12/2010 | Zinn et al. |
| 7,850,675 B2 | 12/2010 | Bell et al. |
| 7,850,705 B2 | 12/2010 | Bach et al. |
| 7,922,757 B2 | 4/2011 | McGuckin |
| 7,972,314 B2 | 7/2011 | Bizup et al. |
| 8,079,973 B2 | 12/2011 | Herrig et al. |
| 8,092,435 B2 | 1/2012 | Beling et al. |
| 8,097,311 B2 | 1/2012 | Wang et al. |
| 8,313,524 B2 | 11/2012 | Edwin et al. |
| 8,512,312 B2 | 8/2013 | Sage |
| 8,690,815 B2 | 4/2014 | Porter et al. |
| 9,278,172 B2 | 3/2016 | Herrig et al. |
| 2001/0053930 A1 | 12/2001 | Kugler et al. |
| 2002/0049403 A1 | 4/2002 | Alanis |
| 2002/0055766 A1 | 5/2002 | Wallace et al. |
| 2002/0055771 A1 | 5/2002 | Sandock |
| 2002/0099432 A1 | 7/2002 | Yee |
| 2002/0151761 A1 | 10/2002 | Viole et al. |
| 2003/0100859 A1 | 5/2003 | Henderson et al. |
| 2003/0135258 A1 | 7/2003 | Andreas et al. |
| 2003/0135261 A1 | 7/2003 | Kugler et al. |
| 2003/0139806 A1 | 7/2003 | Haverkost et al. |
| 2003/0181969 A1 | 9/2003 | Kugler et al. |
| 2003/0212385 A1 | 11/2003 | Brenner et al. |
| 2003/0212431 A1 | 11/2003 | Brady et al. |
| 2003/0229365 A1 | 12/2003 | Whayne et al. |
| 2004/0024442 A1 | 2/2004 | Sowinkski et al. |
| 2004/0073282 A1 | 4/2004 | Stanish |
| 2004/0078071 A1 | 4/2004 | Escamilla et al. |
| 2004/0099395 A1 | 5/2004 | Wang et al. |
| 2004/0147866 A1 | 7/2004 | Blatter et al. |
| 2004/0193242 A1 | 9/2004 | Lentz et al. |
| 2004/0215337 A1 | 10/2004 | Hain et al. |
| 2004/0236412 A1 | 11/2004 | Brar |
| 2005/0004553 A1 | 1/2005 | Douk |
| 2005/0137614 A1 | 6/2005 | Porter et al. |
| 2005/0192559 A1 | 9/2005 | Michels et al. |
| 2005/0192604 A1 | 9/2005 | Carson et al. |
| 2005/0203457 A1 | 9/2005 | Smego |
| 2005/0209581 A1 | 9/2005 | Butts et al. |
| 2005/0215938 A1 | 9/2005 | Khan et al. |
| 2005/0273162 A1 * | 12/2005 | Laguna ............. A61F 2/856 623/1.53 |
| 2006/0004392 A1 | 1/2006 | Amarant |
| 2006/0058867 A1 | 3/2006 | Thistle et al. |
| 2006/0064159 A1 | 3/2006 | Porter et al. |
| 2006/0081260 A1 | 4/2006 | Eells et al. |
| 2006/0118236 A1 | 6/2006 | House et al. |
| 2007/0078412 A1 | 4/2007 | McGuckin, Jr. et al. |
| 2007/0078416 A1 | 4/2007 | Eliasen |
| 2007/0078438 A1 | 4/2007 | Okada |
| 2007/0088336 A1 | 4/2007 | Dalton |
| 2007/0123811 A1 | 5/2007 | Squitieri |
| 2007/0135775 A1 | 6/2007 | Edoga et al. |
| 2007/0142850 A1 | 6/2007 | Fowler |
| 2007/0161958 A1 | 7/2007 | Glenn |
| 2007/0167901 A1 | 7/2007 | Herrig et al. |
| 2007/0168019 A1 | 7/2007 | Amplatz et al. |
| 2007/0173868 A1 | 7/2007 | Bachinski et al. |
| 2007/0191779 A1 | 8/2007 | Shubayev et al. |
| 2007/0197856 A1 | 8/2007 | Gellman et al. |
| 2007/0213838 A1 | 9/2007 | Hengelmolen |
| 2007/0219510 A1 | 9/2007 | Zinn et al. |
| 2007/0233018 A1 | 10/2007 | Bizup et al. |
| 2007/0249986 A1 | 10/2007 | Smego |
| 2007/0249987 A1 | 10/2007 | Gertner |
| 2007/0265584 A1 | 11/2007 | Hickman et al. |
| 2007/0293823 A1 | 12/2007 | Sherry |
| 2007/0293829 A1 | 12/2007 | Conlon et al. |
| 2008/0009781 A1 | 1/2008 | Anwar et al. |
| 2008/0027534 A1 | 1/2008 | Edwin et al. |
| 2008/0132924 A1 | 6/2008 | McGuckin |
| 2008/0167595 A1 | 7/2008 | Porter et al. |
| 2008/0195125 A1 | 8/2008 | Hoffman |
| 2008/0221469 A1 | 9/2008 | Shevchuk |
| 2008/0306580 A1 | 12/2008 | Jenson et al. |
| 2009/0076587 A1 | 3/2009 | Cully et al. |
| 2009/0099649 A1 * | 4/2009 | Chobotov ............. A61F 2/07 623/1.36 |
| 2009/0137944 A1 | 5/2009 | Haarala et al. |
| 2009/0179422 A1 | 7/2009 | Werth |
| 2009/0227932 A1 | 9/2009 | Herrig |
| 2009/0234267 A1 | 9/2009 | Ross |
| 2009/0318895 A1 | 12/2009 | Lachner |
| 2010/0160847 A1 | 6/2010 | Braido et al. |
| 2010/0161040 A1 | 6/2010 | Braido et al. |
| 2010/0198079 A1 | 8/2010 | Ross |
| 2010/0268188 A1 | 10/2010 | Hanson |
| 2010/0268196 A1 | 10/2010 | Hastings et al. |
| 2011/0015723 A1 | 1/2011 | Batiste et al. |
| 2011/0034886 A1 * | 2/2011 | Elbe ............. A61M 39/0208 604/288.01 |
| 2011/0054312 A1 | 3/2011 | Bell et al. |
| 2011/0112482 A1 | 5/2011 | Redd |
| 2011/0208218 A1 | 8/2011 | Ball |
| 2011/0257609 A1 | 10/2011 | Bizup et al. |
| 2011/0264080 A1 | 10/2011 | Lim et al. |
| 2011/0295181 A1 | 12/2011 | Dann et al. |
| 2012/0059305 A1 | 3/2012 | Akingba |
| 2012/0065652 A1 | 3/2012 | Cully et al. |
| 2012/0078202 A1 | 3/2012 | Beling et al. |
| 2012/0143141 A1 | 6/2012 | Verkaik et al. |
| 2013/0060268 A1 | 3/2013 | Herrig |
| 2013/0282108 A1 | 10/2013 | Houston et al. |
| 2013/0338559 A1 | 12/2013 | Franano et al. |
| 2014/0018721 A1 | 1/2014 | Gage et al. |
| 2014/0192567 A1 | 7/2014 | Balocco |
| 2014/0276215 A1 | 9/2014 | Nelson |
| 2014/0288638 A1 | 9/2014 | Knight et al. |
| 2015/0051532 A1 | 2/2015 | Tomko et al. |
| 2015/0094744 A1 | 4/2015 | Aghayev et al. |
| 2016/0129177 A1 | 5/2016 | Herrig |
| 2018/0078745 A1 | 3/2018 | Gray et al. |
| 2020/0178969 A1 | 6/2020 | Hall et al. |

FOREIGN PATENT DOCUMENTS

| | | |
|---|---|---|
| DE | 102008055587 | 8/2009 |
| EP | 0540834 | 5/1993 |
| EP | 1797831 | 6/2007 |
| JP | 5714358 | 1/1982 |
| JP | 62112567 | 5/1987 |
| JP | 04507050 | 12/1992 |
| JP | 05212107 | 8/1993 |
| JP | 06105798 | 4/1994 |
| JP | 0984871 | 3/1997 |
| JP | 09264468 | 7/1997 |
| JP | 2003501223 | 1/2003 |
| JP | 2008511414 | 4/2008 |
| WO | 198403036 | 8/1984 |
| WO | 1990085509 | 8/1990 |
| WO | 199519200 | 7/1995 |
| WO | 199624399 | 8/1996 |
| WO | 1998034676 | 8/1998 |
| WO | 2000027299 | 5/2000 |
| WO | 200076577 | 12/2000 |
| WO | 200105447 | 1/2001 |
| WO | 200105463 | 1/2001 |
| WO | 2001005463 | 1/2001 |
| WO | 2001028456 | 4/2001 |
| WO | 2004032991 | 4/2004 |
| WO | 2004112880 | 12/2004 |
| WO | 2006026687 | 9/2006 |

(56) References Cited

FOREIGN PATENT DOCUMENTS

| WO | 2009046994 | 4/2009 |
|---|---|---|
| WO | 2009059371 | 5/2009 |
| WO | 2010059102 | 5/2010 |
| WO | 2011060386 | 5/2011 |
| WO | 2011153302 | 12/2011 |
| WO | 2012125927 | 9/2012 |
| WO | WO-2015127254 A1 * | 8/2015 |

OTHER PUBLICATIONS

European Search Report dated Dec. 3, 2013 for EP05793066.1.
International Preliminary Report dated Mar. 12, 2014 for PCT/US2012/053967.
International Search Report and Written Opinion dated Jan. 28, 2015 for PCT/US2014/049547.
International Search Report and Written Opinion dated Feb. 19, 2018 for PCT/US2017/060848.
International Search Report and Written Opinion dated Mar. 15, 2013 for PCT/US2012/053967.
International Search Report and Written Opinion dated May 3, 2013 for PCT/US2012/053967.
International Search Report and Written Opinion dated May 6, 1998 for PCT/US1998/001939.
International Search Report and Written Opinion dated Jun. 3, 2009 for PCT/US2009/035923.
International Search Report and Written Opinion dated Jun. 20, 2007 for PCT/US2006/044564.
Notice of Allowance dated Mar. 15, 2010 for U.S. Appl. No. 11/216,536.
Notice of Allowance dated Oct. 4, 2013 for U.S. Appl. No. 12/831,092.
Office Action dated Jan. 9, 2018 for U.S. Appl. No. 14/450,468.
Office Action dated Feb. 6, 2013 for U.S. Appl. No. 12/831,092.
Office Action dated Feb. 21, 2017 for U.S. Appl. No. 14/192,567.
Office Action dated Mar. 15, 2018 for U.S. Appl. No. 14/332,091.
Office Action dated May 5, 2010 for U.S. Appl. No. 10/962,200.
Office Action dated Jun. 9, 2016 for U.S. Appl. No. 14/192,567.
Office Action dated Jun. 15, 2017 for U.S. Appl. No. 14/192,567.
Office Action dated Aug. 7, 2017 for U.S. Appl. No. 14/450,468.
Office Action dated Aug. 12, 2010 for U.S. Appl. No. 10/962,200.
Office Action dated Aug. 15, 2016 for U.S. Appl. No. 14/332,091.
Office Action dated Sep. 20, 2012 for U.S. Appl. No. 12/831,092.
Office Action dated Oct. 27, 2015 for U.S. Appl. No. 14/192,567.
Office Action dated Nov. 26, 2007 for U.S. Appl. No. 10/962,200.
Office Action dated Dec. 5, 2017 for U.S. Appl. No. 14/995,270.
Office Action dated Dec. 20, 2017 for U.S. Appl. No. 14/192,567.
Office Action dated Dec. 30, 2016 for U.S. Appl. No. 14/450,468.
'Clinical Reveiw of MTI, Onxy Liquid Embolization System, available at http://www.fda.gov/ohrms/dockets/ac/03/briefing/3975b1-02-clinical-review pdf. accessed Aug. 29, 2005.
Gore Hybrid Product Brochure—Optimal Outflow wtih Expanded Treatment Options, ,Jan. 2013.
Besarab, et al., Measuring the Adequacy of Hemodialysis Access, Current Opinion in Nephrology and Hypertension, Rapid Science Publishers ISSN ,1996 ,1062-4821.
Coulson MD, et al., Modification of Venous End of Dialysis Grafts: An Attempt to Reduce Neointimal Hyperplasia, Dialysis & Transplantation, vol. 29 No. 1 ,Jan. 2000 ,10-18.
Coulson MD, PhD, et al., A Combination of the Elephant Trunk Anastomosis Technique and Vascular Clips for Dialysis Grafts, Surgical Rounds ,Nov. 1999 ,596-608.
Kanterman, et al., Dialysis Access Grafts: Anatomic Location of Venous Stenosis and Results of Angioplasty, Interventional Radiology, vol. 195 No. 1, 195 ,Apr. 1995 ,135-139.
Kumpe, et al., Angioplasty/Thrombolytic Treatment of Failing and Failed Hemodialysis Access Sites: Comparison with Surgical Treatment, Progress in Cardiovascular Diseases, vol. XXXIV No. 4 ,Jan./Feb. 1992 ,263-278.
Lin, et al., Contemporary Vascular Access Surgery for Chronic Haemodialysis, They Royal College of Surgeons of Edinburgh, J.R. Coll, Surg, Edinb., 41 ,Jun. 1996 ,164-169.
Peterson, et al., Subclavian Venous Stenosis: A Complication of Subclavian Dialysis, The Journal of American Medical Association, vol. 252 No. 24 ,Dec. 28, 1994 ,3404-3406.
Raju M.D., et al., Techniques for Insertion and Management of Complications, PTFE Grafts for Hemodialysis Access, Ann. Surg., vol. 206 No. 5 ,Nov. 1987 ,666-673.
Sharafuddin et al., Percutaneous Balloon-Assisted Aspiration Thrombectomy of clotted ahemodialysis Access Grafts, Journal of Vascular and Interventional Radiology, vol. 7 No 2 ,Mar.-Apr. 1996 ,177-183.
Notice of Allowance dated Sep. 24, 2019 for U.S. Appl. No. 15/807,983.
International Search Report and Written Opinion dated Jul. 17, 2018 for PCT/US2018/023956.
Office Action dated Apr. 16, 2020 for U.S. Appl. No. 15/868,313.
Notice of Allowance dated Oct. 2, 2020 for U.S. Appl. No. 15/933,815.
Office Action dated Oct. 1, 2020 for U.S. Appl. No. 15/868,313.
European Search Report dated Oct. 28, 2020 for EP18771028.0.
Office Action dated Apr. 27, 2021 for U.S. Appl. No. 15/868,313.
Office Action dated Nov. 19, 2021 for U.S. Appl. No. 15/868,313.

* cited by examiner

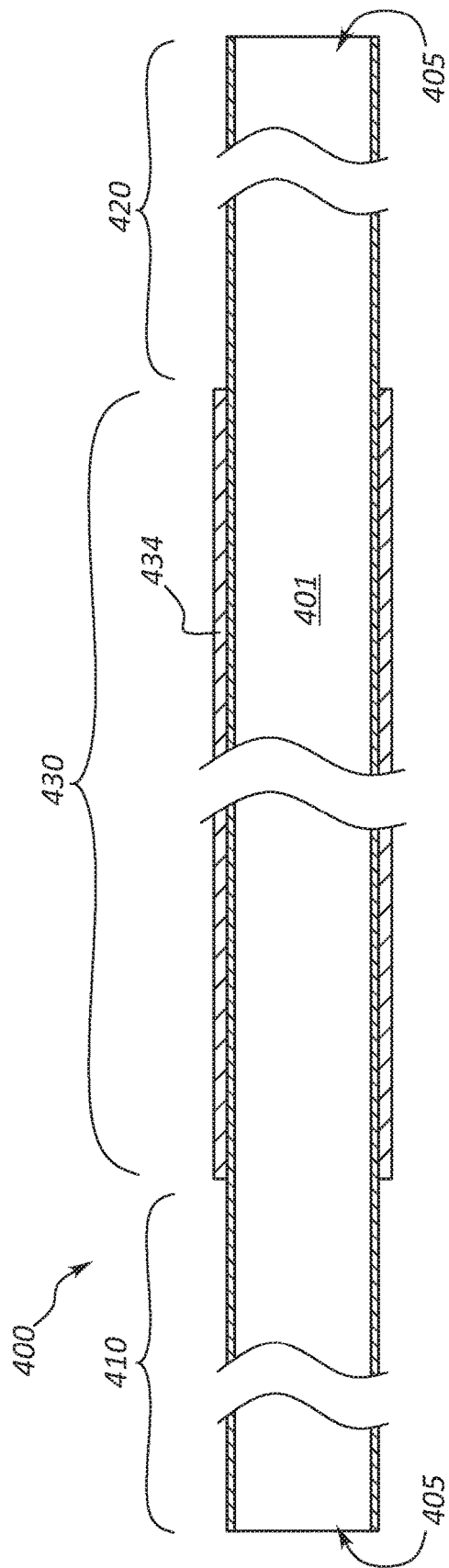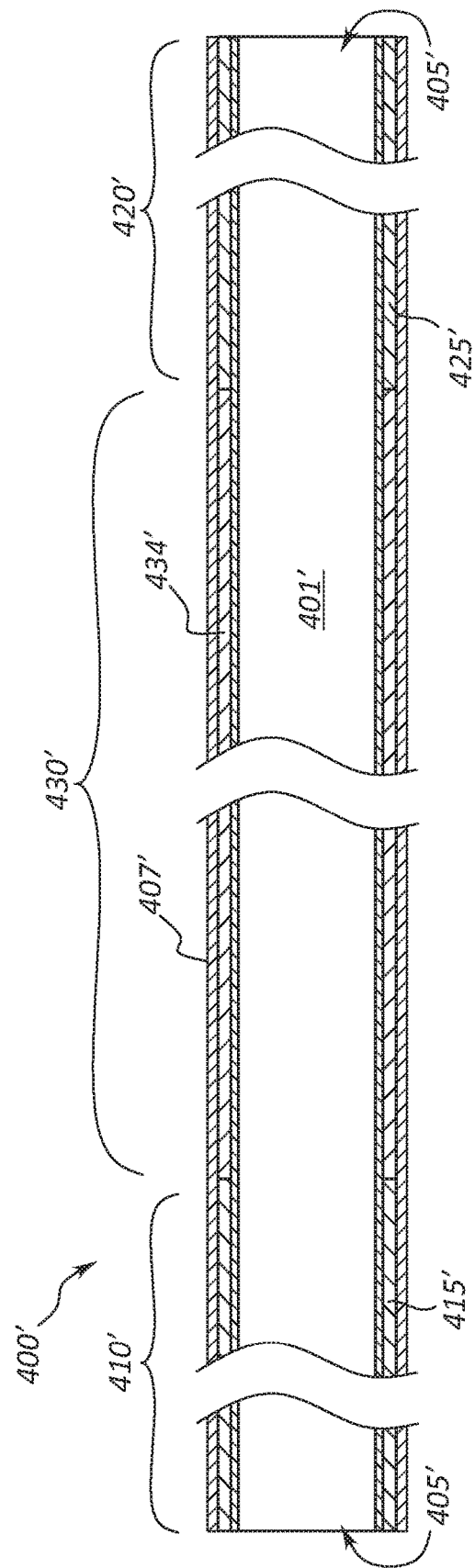

SUBCUTANEOUS VASCULAR ASSEMBLIES FOR IMPROVING BLOOD FLOW AND RELATED DEVICES AND METHODS

RELATED APPLICATIONS

This application claims priority to U.S. Provisional Application No. 62/476,124, filed on Mar. 24, 2017 and titled, "SUBCUTANEOUS VASCULAR ASSEMBLIES FOR IMPROVING BLOOD FLOW AND RELATED DEVICES AND METHODS," and U.S. Provisional Application No. 62/476,151, filed on Mar. 24, 2017 and titled, "SUBCUTANEOUS VASCULAR ASSEMBLIES FOR IMPROVING BLOOD FLOW AND RELATED DEVICES AND METHODS," both of which are hereby incorporated by reference in their entireties.

TECHNICAL FIELD

The present disclosure relates generally to the field of medical devices. More particularly, some embodiments relate to medical assemblies and devices for improving blood flow to regions of a patient's body.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 11A is a cross-sectional side view of the medical device of FIG. 10.

FIG. 11B is a cross-sectional side view of a medical device, according to another embodiment.

DETAILED DESCRIPTION

Figure 1:
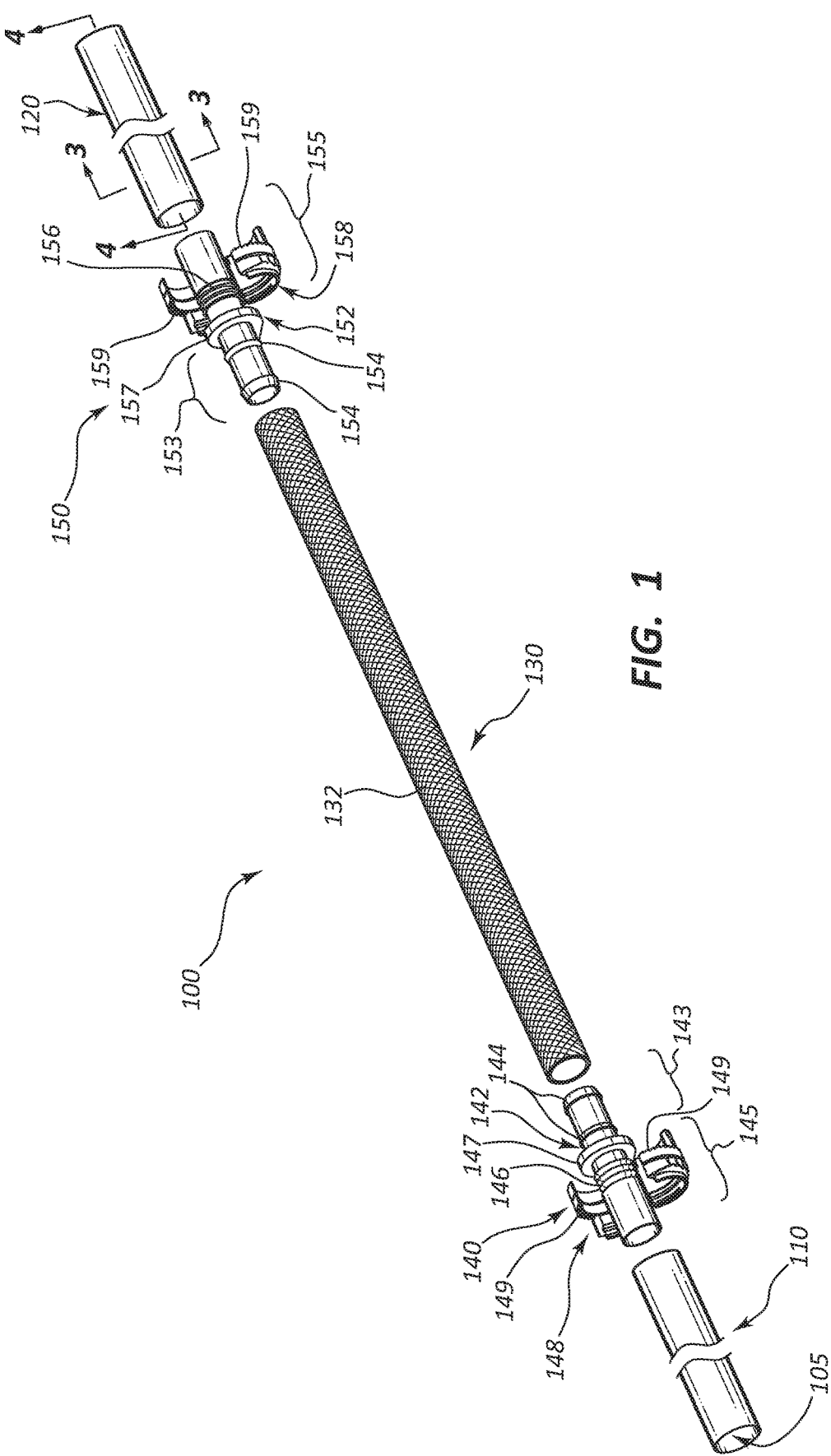
FIG. 1 is an exploded perspective view of a medical device.

Many individuals suffer from insufficient blood flow to regions (e.g., peripheral regions) of their body. For example, some individuals suffering from peripheral artery disease experience narrowing of one or more peripheral arteries (e.g., a superficial femoral artery) to their leg(s) or arm(s). Such narrowing of the arteries may reduce blood flow to one or more peripheral regions. Insufficient blood flow to the extremities of the body can lead to critical limb ischemia, gangrene, and/or amputation. Diabetes is known to increase the risk of peripheral artery disease.

Insufficient blood flow to peripheral regions of a body may result from other causes as well. For example, in addition to atherosclerosis in peripheral arteries, blood flow to a peripheral region may be impeded by some other blockage. In other cases, a portion of an artery may be punctured or weakened, thereby rendering the artery (or a portion of the artery) unsuitable for providing long-term blood flow to a peripheral region.

Embodiments described herein may be used to form a non-natural flow path that improves blood flow to regions of a patient. For example, in some embodiments, a medical device that includes a first graft portion, a second graft portion, and a catheter portion that is coupled to and disposed between the first graft portion and the second graft portion may be inserted into a patient such that the first graft portion is attached to vasculature at a first location that is above the knee of a patient and the second graft portion is attached to vasculature at a second location that is below the knee of the patient. The new flow path that is established between the first location and the second location may improve blood flow to a region (e.g., the lower leg or feet) of the patient.

The components described herein may additionally or alternatively be used to establish other non-natural flow paths within a patient. In some embodiments, both ends of the non-natural flow path are attached to vasculature of the patient. In other embodiments, only one end of the non-natural flow path is attached to vasculature of the patient. In some embodiments, the non-natural flow path is disposed within the torso region of the patient. In other embodiments, the non-natural flow path is disposed below the waist. In some embodiments, the non-natural flow path extends from above the waist to below the waist. In some embodiments, the non-natural flow path traverses the knee (i.e., connects the upper leg with the lower leg). In some embodiments, one end of the non-natural flow path empties directly into a chamber of the heart. Other suitable locations for non-natural flow paths formed by medical devices described herein are possible and within the scope of this disclosure.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Thus, two components may be coupled to each other even though they are not in direct contact with each other. For example, two components may be coupled to one another through an intermediate component. The phrase "attached to" refers to interaction between two or more entities which are in direct contact with each other and/or are separated from each other only by a fastener of any suitable variety (e.g., an adhesive).

As used herein, the term "crush force" refers to the magnitude of a two-dimensional force (e.g., pinch force) that is applied perpendicular to the longitudinal axis of a tube that causes deformation of the tube from an unconstrained state to a constrained state in which the distance between opposite sides of the tube is three quarters of the distance between opposite sides of the tube when the tube is unconstrained. As used herein, the term "hoop force" refers to the magnitude of a force that is uniformly applied around a circumference of a tube to compress the tube to three quarters of its initial diameter. A "medial" portion of a graft is a portion of the graft that is oriented toward the catheter portion of the medical device. The "lateral" portion of a graft is a portion of the graft that is oriented away from the catheter portion of the medical device. In other words, the medial portion of a graft is positioned closer to the catheter portion than is the lateral portion of the graft when the medical device is in a fully assembled configuration. A "porous tube" is considered to be porous even if the porous tubular structure is coated, disposed between, or embedded within a non-porous polymer. For example, a tubular wire structure that includes openings between adjacent elements of wire is porous even if the tubular wire structure is coated, disposed between, or embedded within a non-porous polymer.

Figure 2:
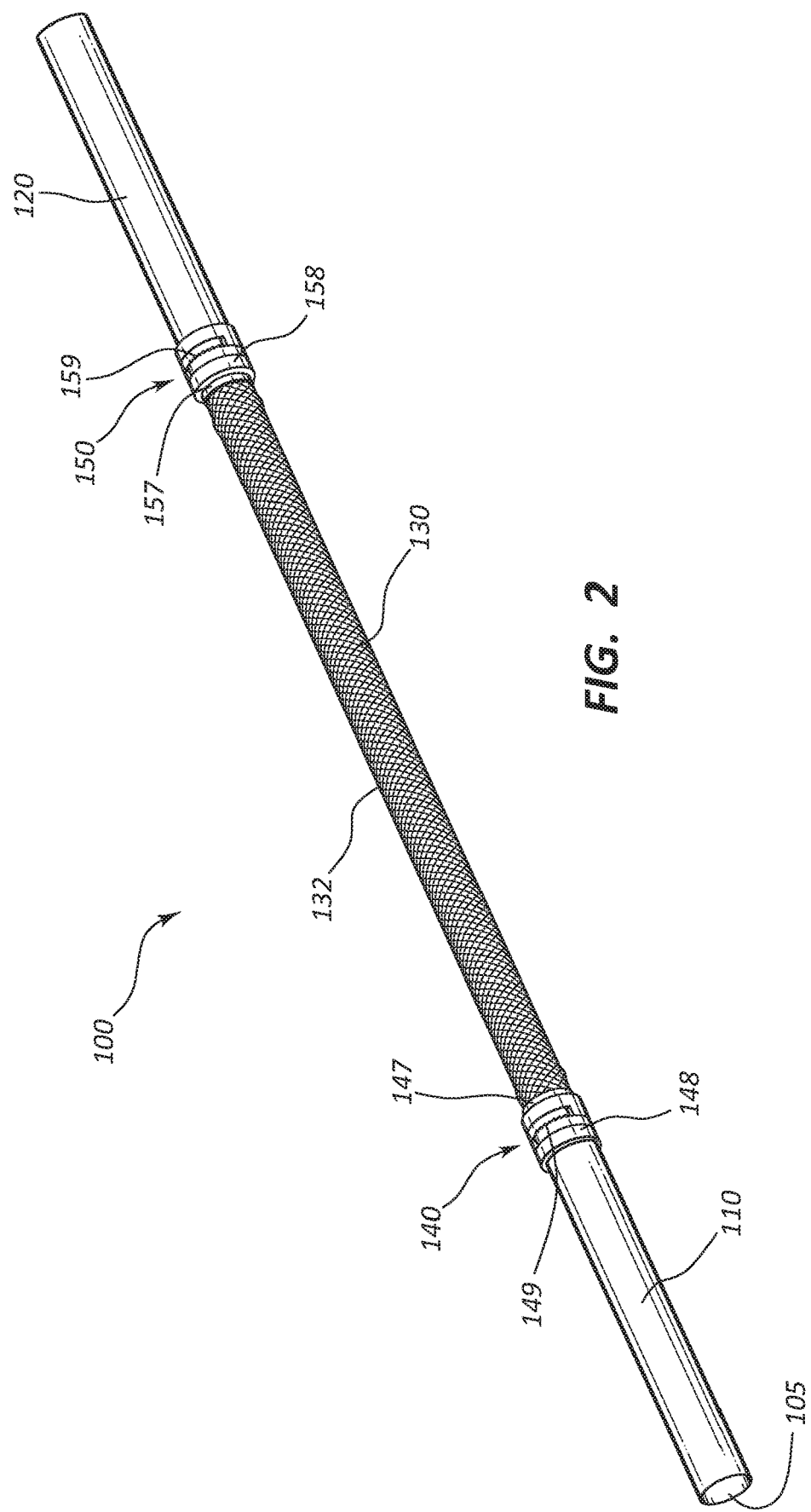
FIG. 2 is an assembled perspective view of the medical device of FIG. 1.
Figure 3:
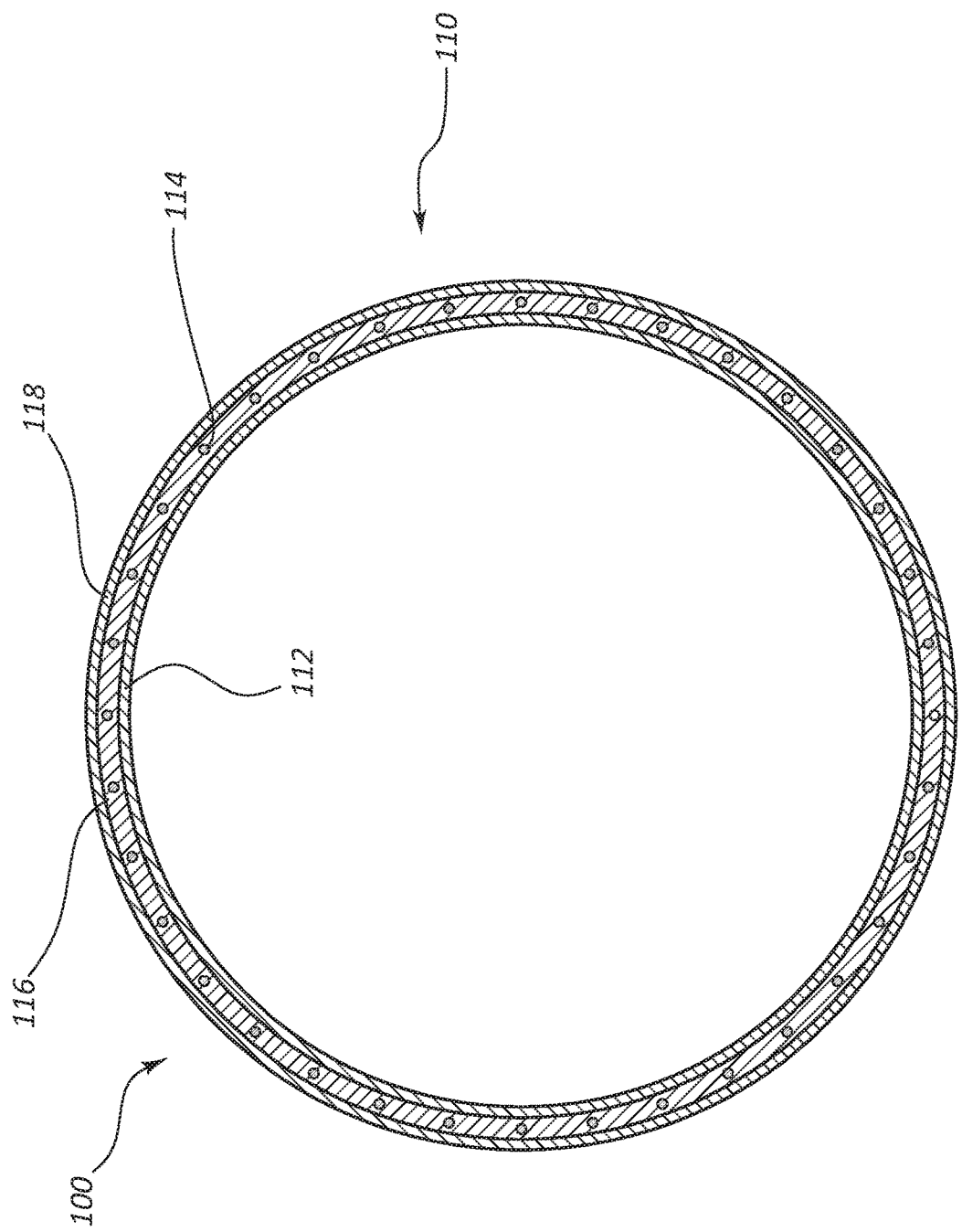
FIG. 3 is a cross-sectional view of a graft of the medical device of FIG. 1 through plane 3-3 of FIG. 1.
Figure 4:
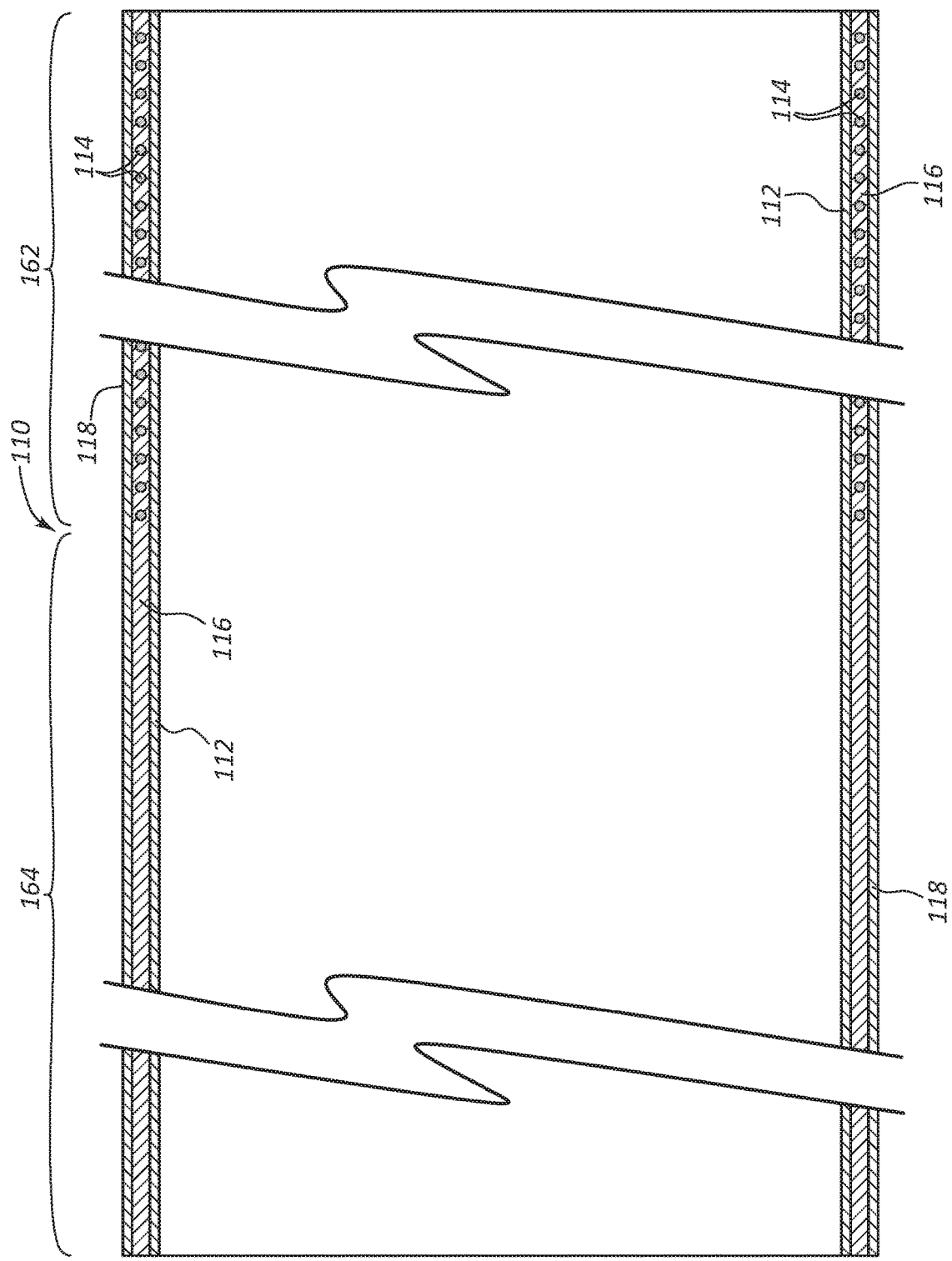
FIG. 4 is a cross-sectional view of a graft of the medical device of FIG. 1 through plane 4-4 of FIG. 1.
Figure 5:
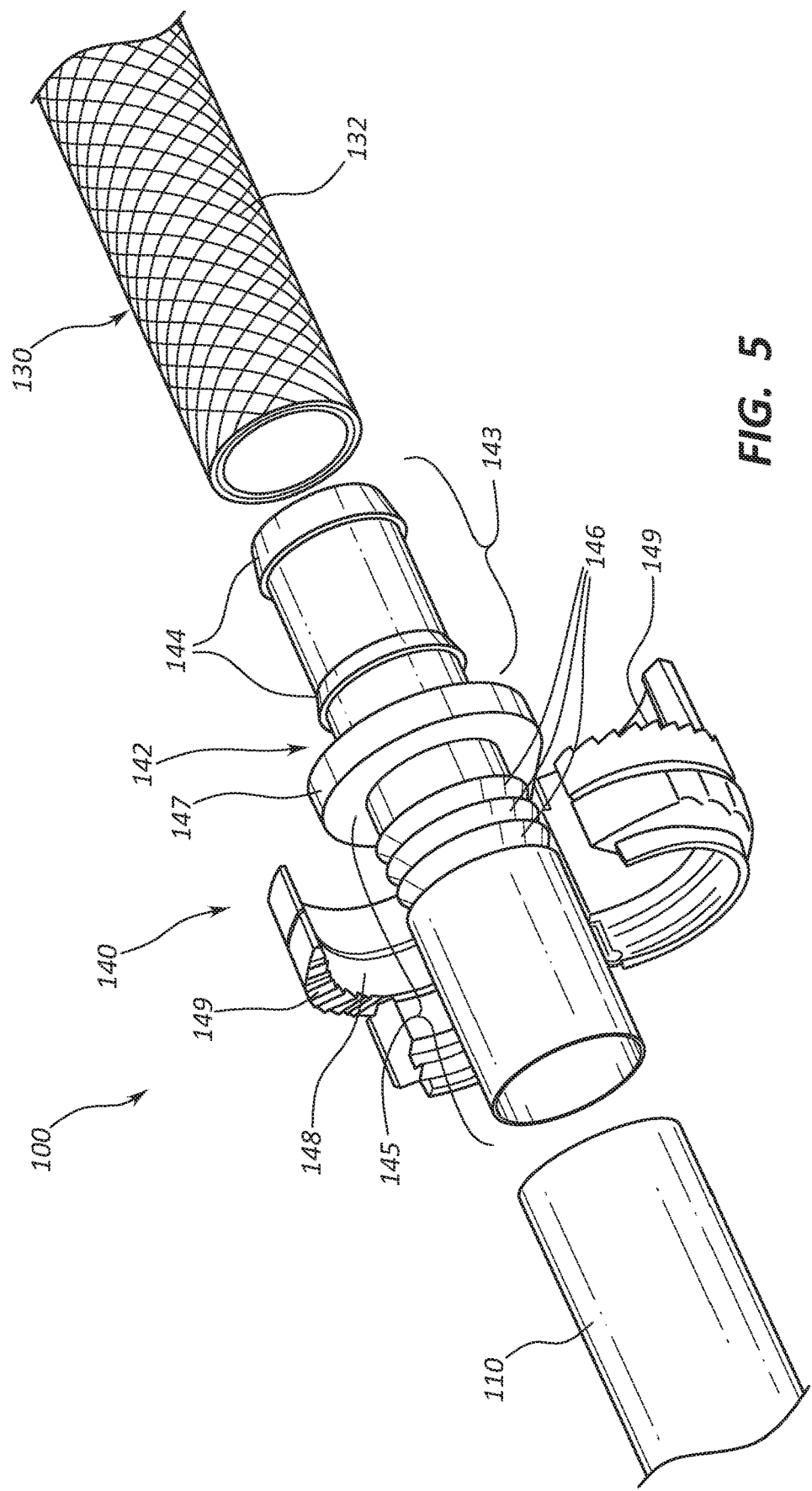
FIG. 5 is a perspective view of a portion of the medical device of FIG. 1.
Figure 6:
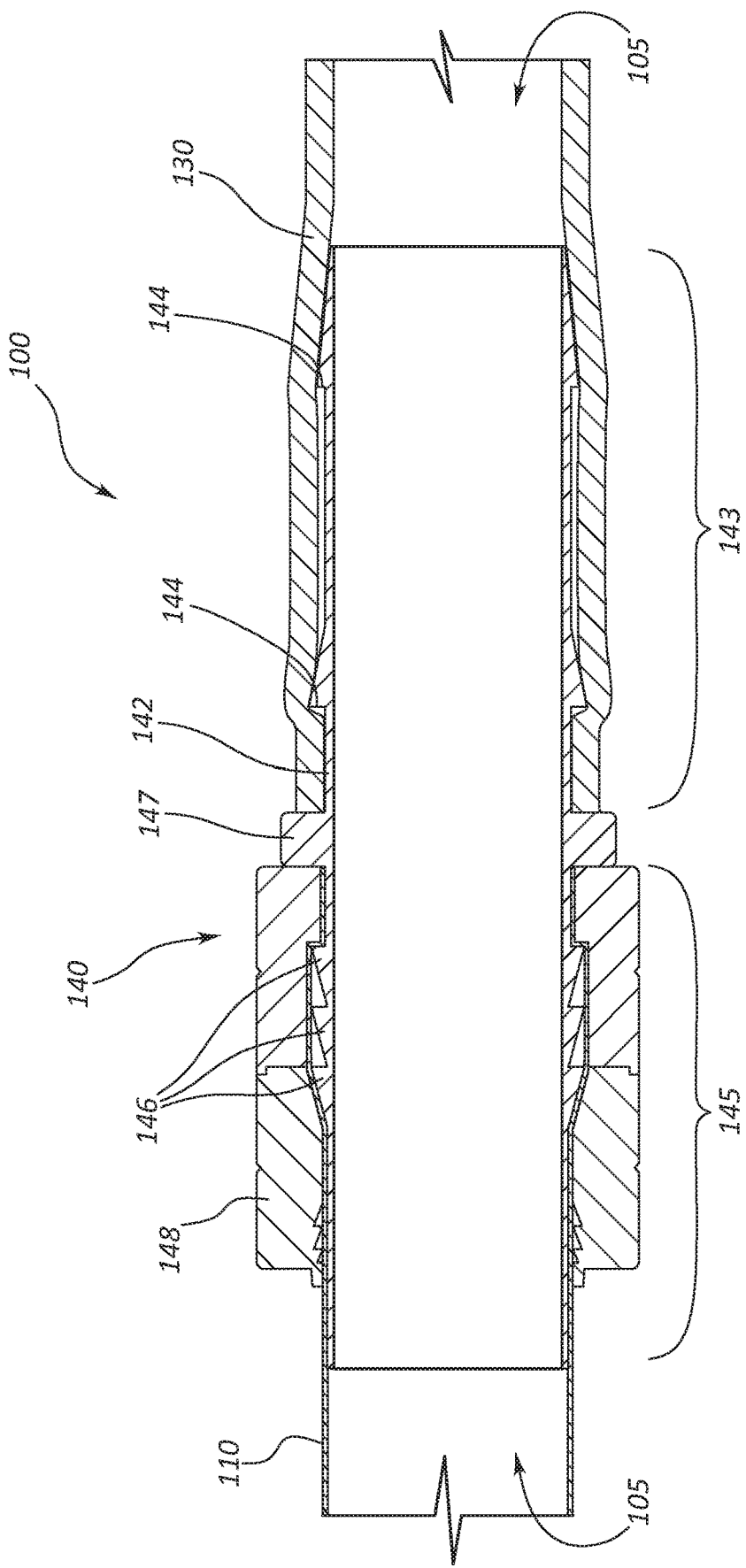
FIG. 6 is a cross-sectional side view of a portion of the medical device of FIG. 1.

FIGS. 1-6 provide alternative views of a medical device 100 (or a portion thereof) for improving blood flow to a region of a patient, such as a lower leg, a foot, an arm, or a hand. More specifically, FIG. 1 provides an exploded perspective view of the medical device 100. FIG. 2 provides an assembled perspective view of the medical device 100. FIG. 3 provides a cross-sectional view of the medical device 100 through plane 3-3 of FIG. 1. FIG. 4 provides a cross-sectional view of a portion of the medical device 100 through plane 4-4 of FIG. 1. FIG. 5 provides a close-up perspective view of a portion of the medical device 100. And FIG. 6 provides a close-up cross-sectional view of the portion of the medical device 100 shown in FIG. 4.

As shown in FIGS. 1-6, the medical device 100 includes first graft portion 110, a second graft portion 120, and a catheter portion 130. The first graft portion 110 may be attached to the catheter portion 130 via a first connector 140, and the second graft portion 120 may be attached to the catheter portion 130 via a second connector 150. Stated differently, the catheter portion 130 may be coupled to and disposed between both the first graft portion 110 and the second graft portion 120. When coupled together, the first graft portion 110, the second graft portion 120, and the catheter portion 130 may together form a lumen 105 that extends across an entirety of the medical device 100. Stated differently, the lumen 105 may extend through the first graft portion 110, the catheter portion 130, and the second graft portion 120.

In some embodiments, the first graft portion 110 and the second graft portion 120 are of the same composition. In other words, in some embodiments, the first graft portion 110 and the second graft portion 120 are made from the same materials. In other embodiments, the first graft portion 110 and the second graft portion 120 differ in composition. In other words, in some embodiments, the first graft portion 110 and the second graft portion 120 may be made, at least in part, from different materials. In some embodiments, the first graft portion 110 and/or the second graft portion 120 are made from relatively flexible materials. The first graft portion 110 and/or the second graft portion 120 may be formed of material that is suitable for anastomosis to a vein or artery of a patient.

In some embodiments, the first graft portion 110 and the second graft portion 120 are the same length, while in other embodiments, the first graft portion 110 and the second graft portion 120 are of different lengths. In some embodiments, the length of the first graft portion 110 and/or the second graft portion 120 is determined by (1) the desired location for placement in the patient and/or (2) the particular anatomy of the patient. For example, the first graft portion 110 and the second graft portion 120 may have lengths that facilitate the bypass of a narrowed, obstructed, and/or damaged portion of an artery or vein.

In some embodiments, the first graft portion 110 and/or the second graft portion 120 comprise multiple layers, as shown in the cross-sectional view of the first graft portion 110 provided in FIG. 3.

For example, in the depicted embodiment, the first graft portion 110 comprises an inner (i.e., luminal) layer 112. The inner layer 112 may be formed from a polymer, such as porous PTFE. More specifically, the inner layer 112 may be formed from expanded PTFE or fibrous PTFE. In embodiments that use fibrous PTFE, the fibrous PTFE may be formed by rotation of a spinneret (i.e., rotational spun PTFE) and/or by subjecting a solution or dispersion comprising PTFE to an electric field (i.e., electrospun PTFE). In some embodiments, the inner layer 112 is configured to permit tissue ingrowth. In some embodiments, the inner layer 112 provides an antithrombic surface and/or an anti-inflammatory surface.

The first graft portion 110 may also include an outer (i.e., abluminal) layer 118. Like the inner layer 112, the outer layer 118 may be formed from a polymer, such as porous PTFE. More specifically, the outer layer 118 may be formed from expanded PTFE or fibrous PTFE. In embodiments that use fibrous PTFE, the fibrous PTFE may be formed by rotation of a spinneret (i.e., rotational spun PTFE) and/or by subjecting a solution or dispersion comprising PTFE to an electric field (i.e., electrospun PTFE). In some embodiments, the outer layer 118 is configured to permit tissue ingrowth. In some embodiments, the outer layer 118 provides an antithrombic surface and/or an anti-inflammatory surface.

In some embodiments, the outer layer 118 is identical in composition to the inner layer 112. In other embodiments, the outer layer 118 and the inner layer 112 differ in composition. In some embodiments, the first graft portion 110 includes fibrous (e.g., rotational spun or electrospun) fluorinated ethylene propylene (FEP).

In some embodiments, the first graft portion 110 includes an intervening layer 116 that is disposed between the inner layer 112 and the outer layer 118. For example, in some embodiments, the intervening layer 116 comprises one or more of silicone, FEP, and polyether block amide (e.g., PEBAX). In some embodiments, the intervening layer 116 is a silicone layer that allows for resealing of the first graft portion 110 after puncture. In other words, in some embodiments, at least a portion of the graft portion 110 may be pierced by a needle or other sharp object. Once the needle or other sharp object is retracted from the graft portion 110, the intervening layer 116 may reseal about the aperture formed by the inserted needle or sharp object, thereby preventing the leakage of blood or other fluid across a wall of the first graft portion 110. Such resealability may permit early cannulation of the first graft portion 110 (e.g., cannulation within one week of implantation).

In some embodiments, one or more layers of the first graft portion 110 may comprise a cell impermeable layer, meaning a layer that is impermeable to migration of at least certain body cells across the layer. For example, the intervening layer 116 (including embodiments wherein the intervening layer comprises silicone) may comprise a cell impermeable layer. In other embodiments a cell impermeable layer may be disposed as an outside layer, an inside layer, or at any point between an outside and an inside layer. Further, cell impermeable layers may be comprised of various materials such as silicone, FEP, or other materials.

In some embodiments, as shown in FIG. 3, the first graft portion 110 may include a porous tube 114 that is partially or completely disposed between the inner layer 112 and the outer layer 118. Stated differently, the porous tube 114 may be disposed between or embedded within one or more layers of polymer. In some embodiments, the porous tube 114 is embedded within the intervening layer 116. The porous tube 114 may strengthen or reinforce the first graft portion 110. For example, in some embodiments, the porous tube 114 is designed to increase the crush force of the first graft portion 110.

In some embodiments, the porous tube 114 comprises and/or consists of a metal alloy. For example, in some embodiments, the porous tube 114 comprises and/or consists of a nickel-titanium alloy, such as nitinol. In some embodiments, the porous tube is formed by winding (e.g., helically wound nitinol) or braiding (e.g., braided nitinol). In other embodiments, the porous tube is formed by laser-cutting (e.g., laser-cut nitinol).

FIG. 4 provides a cross-sectional side view of the first graft portion 110. As shown in FIG. 4, the porous tube 114—in some embodiments—extends across only a portion of the length of the first graft portion 110. For example, in some embodiments, the porous tube 114 extends across only a medial portion 162 of the first graft portion 110, but does not extend to a lateral portion 164 of the first graft portion 110. Stated differently, the first graft portion 110 may include a medial portion 162 and a lateral portion 164, wherein the medial portion 162 comprises the porous tube 114 and the lateral portion 164 is devoid of the porous tube 114. The medial portion 162 of the first graft portion 110 may have a crush force that is greater than a crush force for the lateral portion 164. In other words, the porous tube 114 may provide additional structural support for the medial portion 162, thereby increasing the crush force of the medial portion 162 relative to the lateral portion 164. The lateral portion 164 may be designed to facilitate anastomosis to vasculature of a patient.

In some embodiments, the crush force and/or hoop force of the porous tube 114 itself may vary across its length. For example, in some embodiments, the porous tube 114 may have a lower crush force and/or hoop force at a lateral end than at a medial end. More specifically, in some embodiments in which the porous tube 114 is a nickel-titanium (e.g., nitinol) braid, the density of the braiding may be less within a lateral portion of the porous tube 114 than within a medial portion of the porous tube 114, thereby causing the lateral end of the porous tube 114 to have a lower crush force and/or hoop force than a medial end of the porous tube 114.

In some embodiments, the first graft portion 110 lacks a porous tube. In some instances, for example, the first graft portion 110 may be a commercially known vascular graft, such as a tri-layer vascular graft having an abluminal layer of expanded PTFE, a luminal layer of expanded PTFE that has been coated with heparin, and an intervening elastomeric layer. Other commercially available grafts may alternatively be used. For example, in some embodiments, the first graft portion 110 may be selected by the practitioner based on its flexibility, tensile strength, stretchiness, size, and/or resistance to kinking, and/or the practitioner's experience with the graft portion 110.

The disclosure set forth above in connection with the first graft portion 110 may apply to the second graft portion 120. Stated differently, the second graft portion 120 may have any of the features discussed above in connection with the first graft portion 110.

In some embodiments, the length(s) of the first graft portion 110 and/or the second graft portion 120 are altered prior to implantation of the medical device 100 into a patient. In some embodiments, the length of the first graft portion 110 and/or the second graft portion 120, when implanted within the patient, is between 2 cm and 40 cm, such as between 2 cm and 10 cm, between 5 cm and 15 cm, between 10 cm and 20 cm, between 15 cm and 25 cm, between 20 cm and 30 cm, between 25 cm and 35 cm, or between 30 cm and 40 cm.

As noted above, the catheter portion 130 of the medical device 100 may be coupled to and disposed between the first graft portion 110 and the second graft portion 120. The catheter portion 130 of the medical device 100 may differ in composition from the first graft portion 110 and the second graft portion 120. In some embodiments, the catheter portion 130 has a crush force that is greater than both the crush force of the first graft portion 110 and the crush force of the second graft portion 120. The high crush force of the catheter portion 130 may prevent or reduce the risk of collapse of the catheter portion 130. In some embodiments, the catheter portion 130 has a hoop force that is greater than both the hoop force of the first graft portion 110 and the hoop force of the second graft portion 120. Due to the relatively high crush force and/or hoop force of the catheter portion 130, the catheter portion 130 may be suited for positioning within a patient where strength and/or crush resistance is warranted. For example, the catheter portion 130 may be designed to be positioned adjacent bones or ligaments that might cause the collapse of lumens that are formed from weaker material. In some embodiments, the catheter portion 130 is positioned adjacent relatively sharp anatomy or in locations in which there is significant movement. In some embodiments, the catheter portion 130 is designed to traverse a relatively sharp bend without kinking. The catheter portion 130 may additionally or alternatively be designed to be positioned at a relatively exposed location that is likely to be subjected to compression forces with some frequency. In short, the catheter portion 130 may be positioned within a patient at a location where strength is warranted and/or along the portion of the flow path that is most likely to fail or necessitate replacement.

In some embodiments, the catheter portion 130 is between 2 cm and 60 cm in length. For example, in some embodiments, the catheter portion is between 10 cm and 50 cm in length, and/or between 15 and 40 cm in length.

In some embodiments, the catheter portion 130 is reinforced by metal or a metal alloy. For example, in some embodiments, the catheter portion 130 includes a porous tube 132 that is made from metal or metal alloy. In some embodiments, the porous tube 132 is made from or comprises a nickel-titanium alloy, such as nitinol. In some embodiments, the porous tube 132 is formed by winding (e.g., wound nitinol) or braiding (e.g., braided nitinol). In other embodiments, the porous tube 132 is formed by laser-cutting (e.g., laser-cut nitinol).

In some embodiments, the porous tube 132 of the catheter portion 130 is disposed within or between one or more polymers. For example, in some embodiments, the porous tube is embedded within silicone, FEP, or polyether block amide. In other embodiments, the porous tube 132 is not embedded within a single layer. For example, in some embodiments, the porous tube 132 is disposed between—but not embedded within—separate polymeric layers. In some instances, the porous tube 132 is luminal of a layer comprising silicone, FEP, or polyether block amide. In other embodiments, the porous tube 132 is abluminal of a layer comprising silicone, FEP, or polyether block amide.

In some embodiments, the catheter portion 130 may comprise at least one layer that is cell impermeable meaning it is impermeable to migration of at least certain body cells across the layer. A cell impermeable layer may comprise silicone, FEP, or other materials. In certain applications, a catheter portion 130 having a cell impermeable layer may be used in connection one or more graft portions (such as first graft portion 110 and/or second graft portion 120) which may comprise cell impermeable layers.

In some embodiments, the catheter portion 130 has a smooth and nonporous exterior surface. The exterior surface may prevent tissue ingrowth, thereby enabling replacement of the catheter portion 130, such as described in greater detail below.

As noted above, connectors, such as the first connector 140 and the second connector 150, may be used to couple the catheter portion 130 to the first graft portion 110 and the second graft portion 120. For instance, the first connector 140 may be used to couple the catheter portion 130 to the first graft portion 110. The second connector 150 may be used to couple the catheter portion 130 to the second graft portion 120. Stated differently, when the medical device 100 is fully assembled and implanted within a patient, the first graft portion 110 may be attached to the catheter portion 130 via a first connector 140 and the second graft portion 120 may be attached to the catheter portion 130 via a second connector 150.

In some embodiments, one or both of the connectors 140, 150 may include an elongate tube 142, 152 and a clamp 148, 158. In some embodiments, the elongate tubes 142, 152 are rigid or substantially rigid structures that are resistant to compression. In some embodiments, the elongate tubes 142, 152 comprise a metal or a metal alloy. In some embodiments, the elongate tubes 142, 152 are configured such that a first portion 143, 153 of the elongate tube 142, 152 may be disposed within an inner diameter of the catheter portion 130 while a second portion 145, 155 of the elongate tube 142, 152 may be disposed within an inner diameter of the first graft portion 110 or the second graft portion 120. Stated differently, each elongate tube 142, 152 may be partially disposed within both the catheter portion 130 and either the first graft portion 110 or the second graft portion 120.

In some embodiments, the first portions 143, 153 of the elongate tubes 142, 152 include one or more protrusions 144, 154 that frictionally engage with the interior diameter of the catheter portion 130. In some embodiments, any attempt to remove the catheter portion 130 from the elongate tube 142, 152 may cause the catheter portion 130 to "neck down" or become narrower in diameter, thereby causing the catheter portion 130 to more tightly engage with the elongate tube 142, 152.

In some embodiments, the second portions 145, 155 of the elongate tubes 142, 152 include one or more protrusions 146, 156 that frictionally engage with the interior diameter of the first graft portion 110 or the second graft portion 120.

In some embodiments, the elongate tubes 142, 152 of connectors 140, 150 include a flange 147, 157. The flange 147, 157 may be designed to separate the catheter portion 130 from either the first graft portion 110 or the second graft portion 120. Stated differently, the flange 147, 157 may be disposed adjacent to and between the catheter portion 130 and either the first graft portion 110 or the second graft portion 120.

The clamps 148, 158 may be designed to provide a compressive force to the first graft portion 110 and/or the second graft portion 120, thereby securing the first graft portion 110 and/or the second graft portion 120 between the elongate tube 142, 152 and the clamps 148, 158. In some embodiments, the clamps 148, 158 are clam-shell clamps that include two separate portions that are hingedly connected to one another. Stated differently, opposite portions of the clamps 148, 158 may be rotated relative to each other to provide a compressive force around the first graft portion 110 or the second graft portion 120. In some embodiments, the opposite portions of clamps 148, 158 lock together as they are rotated toward one another. For example, in some embodiments, teeth 149, 159 on the opposite portions of the clamps 148, 158 interlock with one another as the clamps 148, 158 are secured over the first graft portion 110 or the second graft portion 120.

In other embodiments, the connectors 140, 150 may couple the first graft portion 110 and/or the second graft portion 120 to the catheter portion 130 in some other way. For example, in some embodiments, the connectors may lack clam-shell clamps.

While the embodiment depicted in FIGS. 1-6 includes a single catheter portion 130 and two graft portions (i.e., the first graft portion 110 and the second graft portion 120), other embodiments may include a different number of catheter portions and/or graft portions. For example, in some embodiments, additional connectors may be used to couple two separate catheter portions to one another. In some embodiments, the graft portions may be branched. In other embodiments, only one graft portion is used. The connectors may be used to mix and match any suitable tubular elements to one another to create a non-natural flow path within a patient. In some embodiments, the flow path may be formed from a plurality of catheters. The connectors provide customizability during a medical procedure, thereby allowing a practitioner to connect any suitable tubular element to any other suitable tubular element, thereby establishing a non-natural flow path.

Some embodiments relate to a kit for establishing a non-natural flow path within a patient. The kit may include, inter alia, the following components: a catheter 130, a first connector 140 for coupling a first graft 110 to the catheter 130, and a second connector 150 for coupling a second graft 120 to the catheter 130. In some embodiments, the kit further includes instructions for implanting the catheter 130, the first graft 110, and the second graft 120 into a patient such that the first graft is coupled to the catheter 130 via the first connector 140 and the second graft 120 is coupled to the catheter 130 via the second connector 150. In some embodiments, the instructions specify that (1) the first graft 110 is to be attached to vasculature of a patient at a location that is above the knee of the patient and (2) the second graft 120 is to be attached to vasculature of the patient at a location that is below the knee of the patient. In some embodiments, the kit further includes a cutting device (e.g., scissors) that is configured for shortening (e.g., cutting) the first graft 110, the second graft 120, and/or the catheter 130.

In some circumstances, the kit may be used with any suitable graft(s). For example, the practitioner may select a first graft 110 and/or a second graft 120 from any suitable graft, such as any of the numerous commercially available grafts. The graft(s) may be selected based on the characteristics desired by the practitioner. For example, the graft(s) may be selected based on their flexibility, tensile strength, stretchiness, size, or resistance to kinking. In other embodiments, the kit includes one or both of the first graft 110 and the second graft 120, wherein the first graft 110 and/or the second graft 120 are coupled to the catheter 130.

The medical device 100, the kits, and/or related components described above may be used to establish a non-natural pathway, such as a pathway that bypasses an occluded, partially occluded, or damaged portion of the vasculature.

Figure 7:
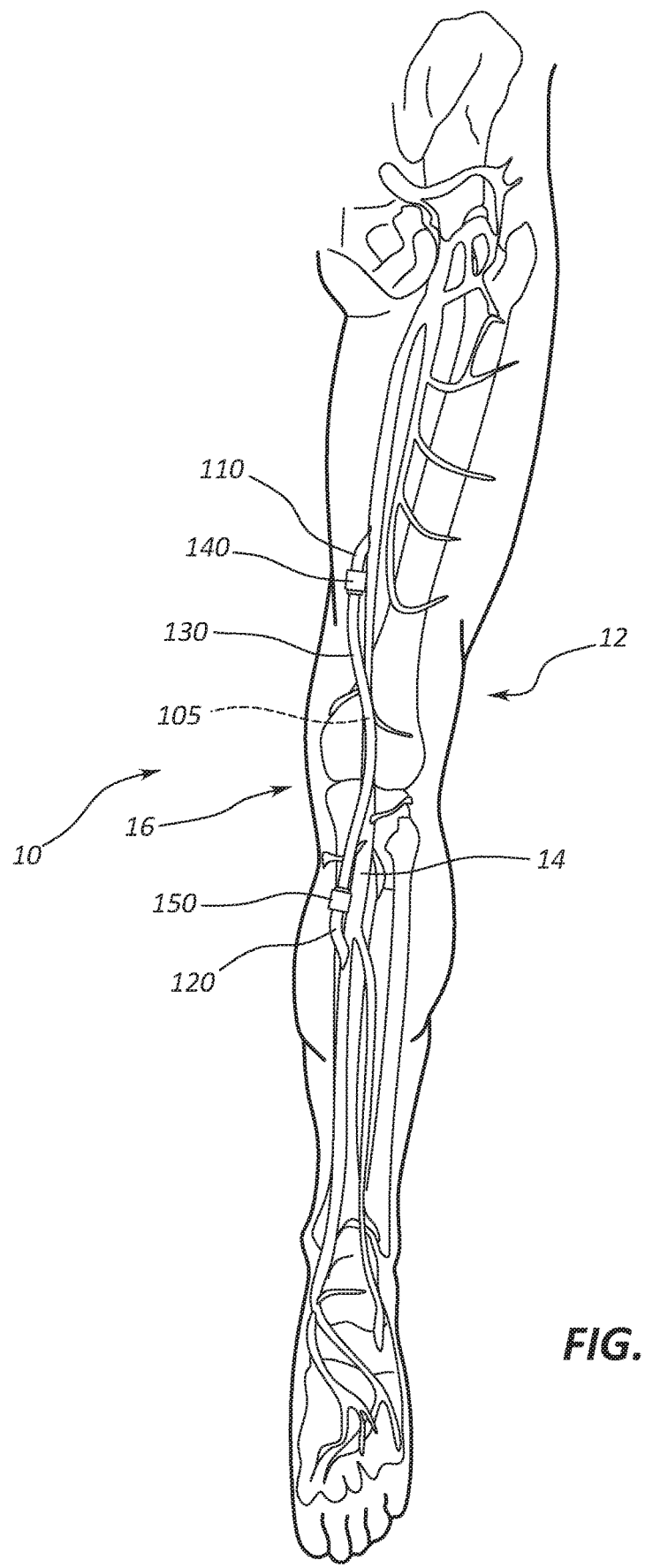
FIG. 7 is a posterior view of a leg of a patient into which the medical device of FIG. 1 has been implanted.

For example, in some embodiments, a practitioner may obtain the components of the medical device 100 described above. The practitioner may then implant the medical device 100 into a patient such that (1) the first graft portion 110 is attached to vasculature of the patient at a first location, (2) the second graft portion 120 is attached to vasculature of the patient at a second location that differs from the first location, and (3) the catheter portion 130 is coupled to and disposed between both the first graft portion 110 and the second graft portion 120. A medical device 100 that has been implanted into a leg 12 of a patient 10 is depicted in FIG. 7. The medical device 100 is implanted such that the first graft 110 is attached to the femoral artery 14 above the knee 16 of the patient 10, while the second graft 120 is attached to the femoral artery 14 below the knee 16 of the patient 10, thereby bypassing a damaged portion of the femoral artery 14. In other embodiments, the medical device 100 is implanted at other locations within the patient 10.

In some embodiments, the first graft portion 110 and the second graft portion 120 are coupled to the catheter portion 130 prior to implantation. Stated differently, the assembled medical device 100 may be inserted into the patient 10 (either percutaneously or through an "open" surgical procedure) and then attached to the vasculature of the patient 10 via anastomosis at the lateral ends of the first graft portion 110 and the second graft portion 120.

In some embodiments, one or more components of the medical device 100 are implanted into the patient 10 before the medical device 100 is fully assembled. For example, in some embodiments, the catheter portion 130 is first implanted (e.g., subcutaneously) into the patient 10. Then one or more of the first graft portion 110 and the second graft portion 120 are attached to the catheter portion 130. In some embodiments, the first graft portion 110 may be attached to the catheter portion 130 by partially inserting the elongate tube 142 of the connector 140 into the catheter portion 130. The catheter portion 130 may be secured to the elongate tube 142 of the connector 140 via a friction fit. The elongate tube 142 of the connector 140 may then be partially inserted into a medial portion of the first graft portion 110. The first graft portion 110 may be secured via placement of the clamp 148. For example, opposite portions of a clam-shell clamp 148 may be rotated toward one another to provide a compressive force around the first graft portion 110. The opposite portions of the clamp 148 may lock together, thereby securing the first graft portion 110 to the catheter portion 130. The second graft portion 120 may be attached to the catheter portion 130 in an analogous manner.

In some embodiments, one or both of the first graft portion 110 and the second graft portion 120 are shortened prior to (1) attachment of the first graft portion 110 to the catheter portion 130 and/or (2) attachment of one or both of the first graft portion 110 and the second graft portion 120 to the vasculature of the patient 10. For example, in some embodiments, a medial portion of the first graft portion 110 is removed to shorten the first graft portion 110 prior to coupling of the first graft portion 110 to the catheter portion 130. In some embodiments, removal of the medial portion may require cutting through the porous tube 114, thereby forming exposed ends (e.g., sharp ends) at the newly formed lateral end of the porous tube 114. The exposed ends of the porous tube 114 may be positioned adjacent the flange 147 of the elongate tube 142. In this manner, the flange 147 may protect the patient 10 and/or other components of the medical device 100 from the exposed ends. The flange 147 may also protect the patient 10 from exposed ends of the catheter portion 130. The flange 157 may operate in an analogous manner.

In some embodiments, a lateral portion of the first graft portion 110 is removed to shorten the first graft portion 110 prior to attachment of the first graft portion 110 to the vasculature of the patient 10. The removal of a lateral portion of the first graft portion 110 may be done before or after the first graft portion 110 has been coupled to the catheter portion 130. In some embodiments, the catheter portion 130 is shortened prior to or during implantation into the patient 10, thereby enabling the practitioner to select the desired length of the catheter portion 130.

In some embodiments, the medical device 100 is implanted without using a deployment device. Stated differently, the medical device 100 may be inserted into the patient 10 without passing through a tubular structure. In other embodiments, the medical device 100 (or components thereof) are implanted through a tubular structure.

When implanted within the patient 10, the first graft portion 110, the second graft portion 120, and the catheter portion 130 may together form the lumen 105 that extends from the first location to the second location. In some embodiments, the surface defining the lumen 105 includes one or more discontinuities. In other embodiments, the lumen is defined by a smooth continuous surface that extends across the first graft portion 110, the second graft portion 120, and the catheter portion 130. Such a smooth and continuous luminal surface may reduce the extent of blood turbulence and clotting (i.e., reduce the extent of thrombus formation).

In some embodiments, the first location and the second location are separated from one another by a distance of more than 5 cm, 10 cm, 15 cm, 20 cm, and/or 30 cm. In some embodiments, the first location is above a knee 16 of the patient 10, while the second location is below the knee 16 of the patient 10. In some embodiments, the first location is the femoral artery 14 and the second location is the popliteal artery. Stated differently, the medical device 100 may be used in a femoropopliteal bypass procedure. In some embodiments, the first location is a first femoral artery that provides blood to a first leg of the patient and the second location is a second femoral artery that provides blood to a second leg of the patient.

In some embodiments, both the first location and the second location are positioned at arteries. Stated differently, the medical device 100 may be used to establish a non-natural flow path between a first portion of an artery and a second portion of an artery. (The first portion of an artery and the second portion of the artery may be different portions of the same artery or reside on different arteries.) In some embodiments, the first location is positioned at an artery and the second location is positioned at a vein. Stated differently, the medical device 100 may be used to establish a non-natural flow path between an artery and a vein. In some embodiments, both the first location and the second location are positioned at a vein. In other words, the medical device 100 may be used to establish a non-natural flow path between a first portion of a vein and a second portion of a vein. (The first portion of a vein and a second portion of a vein may be different portions of the same vein or reside on different veins.)

In some embodiments, the patient is selected for implantation based on a diagnosis of an occluded, partially occluded, or damaged blood vessel. Stated differently, the medical device 100 may be implanted into an individual to bypass an occluded, partially occluded, or damaged blood vessel, thereby establishing a non-natural flow path to improve the flow of blood to a region (e.g., a peripheral region) of the patient's body.

In some embodiments, the catheter portion 130 of the medical device 100 may be removed from the patient 10 without removing the first graft portion 110 and/or the second graft portion 120.

For example, in some embodiments, the practitioner may make an incision in a patient 10 to provide access to at least a portion of the medical device 100 which had been previously implanted into the patient 10. In some embodiments, the catheter portion 130 of the medical device 100 may be made from material that is resistant to tissue ingrowth, while one or both of the first graft portion 110 and the second graft portion 120 permit tissue ingrowth. Stated differently the tissue of the patient 10 may be intimately connected with the first graft portion 110 and the second graft portion 120, but less intimately associated with the catheter portion 130. In some instances, at the time of the removal procedure, the medical device 100 had been implanted into the patient 10 for at least one week, one month, and/or one year. Once the practitioner has established access with at least a portion of the medical device 100, the catheter portion 130 may then be uncoupled from the first graft portion 110 and the second graft portion 120. For example, in some embodiments, the connectors 140, 150 may be unlocked and/or released, thereby allowing the first graft portion 110 and the second graft portion 120 to be uncoupled from the elongate tubes 142, 152 of the connectors 140, 150. Once uncoupled from the first graft portion 110 and the second graft portion 120, the catheter portion 130 may then be removed from the patient 10. A second catheter portion (not shown) may then be coupled to the first graft portion 110 and the second graft portion 120 while the first graft portion 110 and the second graft portion 120 remain attached to vasculature of the patient 10. Such attachment may be accomplished via any suitable connector, such as the connectors 140, 150 described herein. In this manner, the catheter portion 130 of the medical device 100 may be replaced without removing the first graft portion 110 and the second graft portion 120 from the patient 10.

Figure 8:
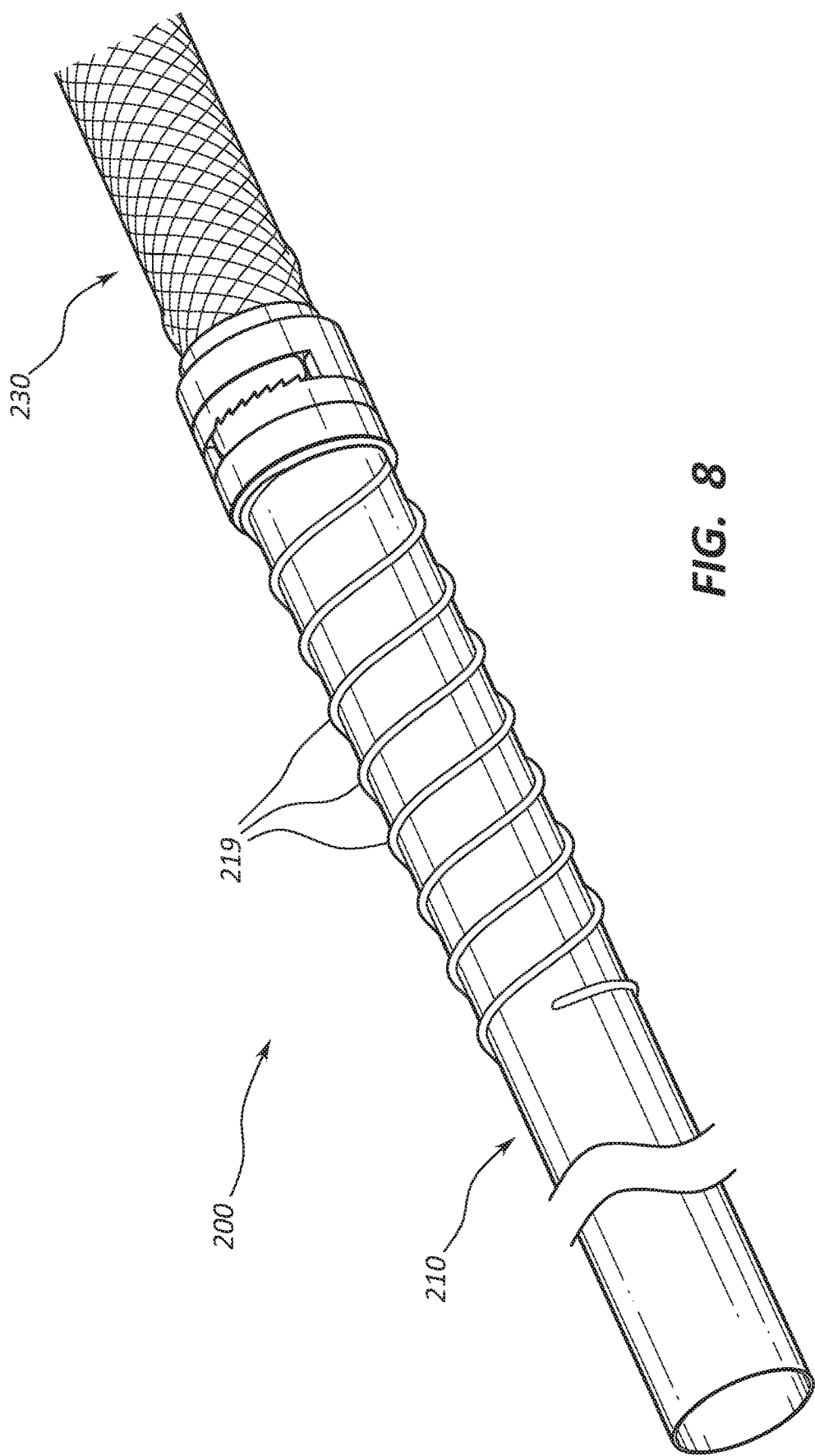
FIG. 8 is a perspective view of a portion of a medical device according to another embodiment.

FIG. 8 depicts an embodiment of a medical device 200 that resembles the medical device 100 described above in certain respects. Accordingly, like features are designated with like reference numerals, with the leading digits incremented to "2." For example, the embodiment depicted in FIG. 8 includes a catheter portion 230 that may, in some respects, resemble the catheter portion 130 of FIGS. 1-7. Relevant disclosure set forth above regarding similarly identified features thus may not be repeated hereafter. Moreover, specific features of the medical device 100 and related components shown in FIGS. 1-7 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the medical device 200 and related components depicted in FIG. 8. Any suitable combination of the features, and variations of the same, described with respect to the medical device 100 and related components illustrated in FIGS. 1-7 can be employed with the medical device 200 and related components of FIG. 8, and vice versa. This pattern of disclosure applies equally to further embodiments depicted in subsequent figures and described hereafter, wherein the leading digits may be further incremented.

FIG. 8 provides a perspective view of a portion of a medical device 200. The view provided in FIG. 8 shows the attachment of a first graft portion 210 to the catheter portion 230. The medical device 200 is identical to the medical device 100 except that the first graft portion 210 further includes beading 219 disposed around an outer surface (e.g., a circumference) of the first graft portion 210 and/or the second graft portion (not shown). In some embodiments, the beading 219 is helical in shape. In some embodiments, the helical beading 219 comprises or consists of PTFE. The beading 219 may reduce the propensity of the first graft portion 210 for kinking. In other words, the beading 219 may lessen the likelihood that the first graft portion 210 will become kinked.

Figure 9:
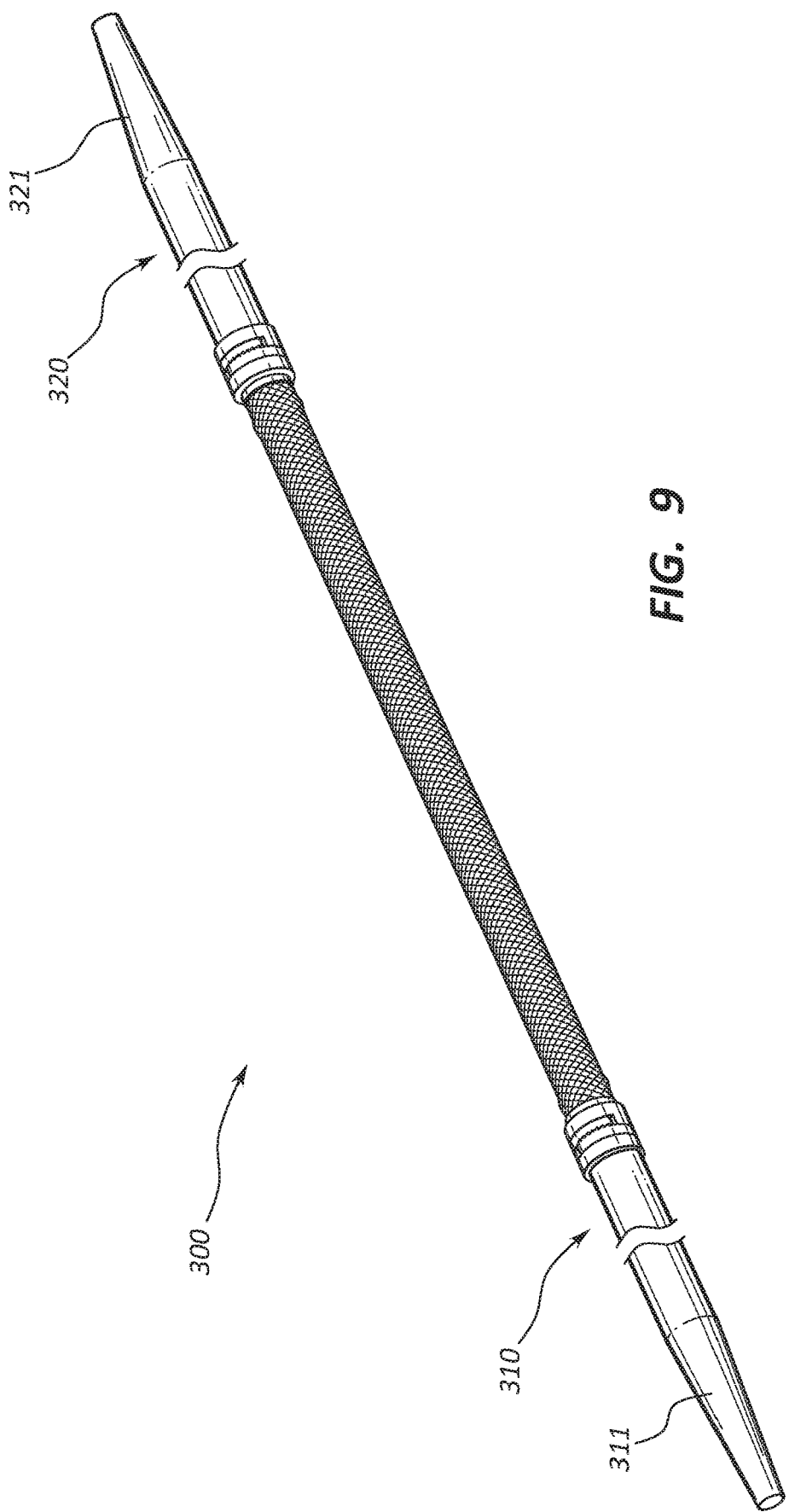
FIG. 9 is a perspective view of a medical device, according to another embodiment.

FIG. 9 depicts another embodiment of a medical device 300. The medical device 300 is generally analogous to the medical devices 100, 200 discussed above, except that the medical device 300 includes one or more tapers 311, 321. For example, in some embodiments, the first graft portion 310 includes a taper 311 such that a lateral portion of the first graft portion 310 is narrower (e.g., has a smaller circumference) than a medial portion of the first graft portion 310. The taper 311 of the first graft portion 310 may be designed to facilitate anastomosis to vasculature at a particular location within a patient. Stated differently, the taper 311 may be selected such that the diameter of a lateral end of the first graft portion 310 closely matches the diameter of vasculature of the patient to which the first graft portion 310 is to be attached. In some embodiments, the first graft portion 310 may taper such that the inner diameter of the first graft portion 310 narrows from the medial end to the lateral end by between 1.5 mm and 5 mm, such as between 2 mm and 4 mm. For example, the first graft portion 110 may taper from an inner diameter of between 6.5 mm and 9 mm at a medial end to an inner diameter at a lateral end that is between 2 and 4 mm smaller. In embodiments in which the second graft portion 320 includes a taper 321, the taper 321 may have any of the features or characteristics discussed above in connection with the taper 311. In other embodiments, one of the first graft portion 310 and the second graft portion 320 includes a taper, but the other does not.

Figure 10:
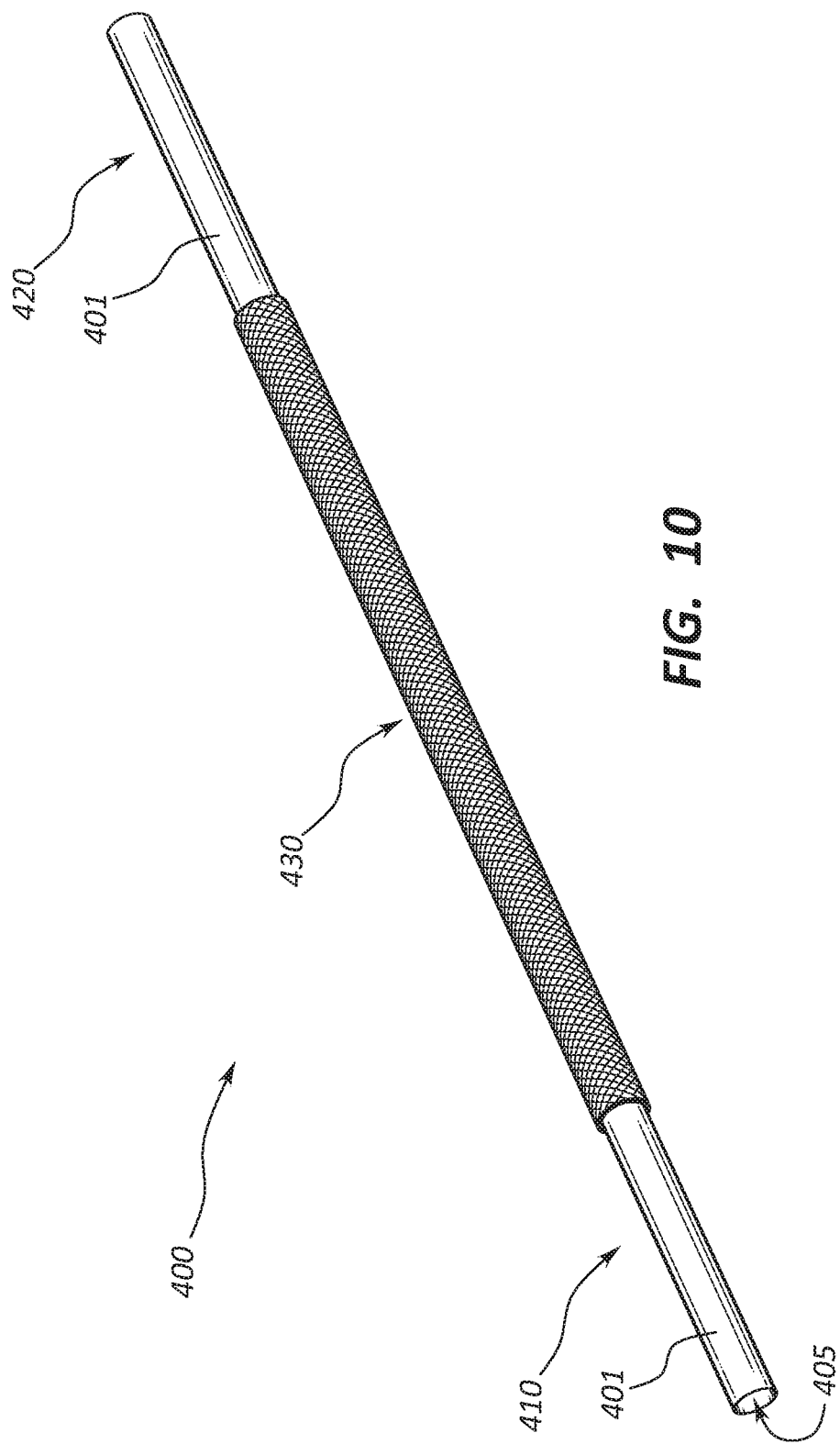
FIG. 10 is a perspective view of a medical device, according to another embodiment.

FIGS. 10-11A depict another embodiment of a medical device 400. The medical device 400 is generally analogous to the medical devices 100, 200, 300 discussed above. However, the medical device 400 differs from the medical devices 100, 200, 300 in that the medical device 400 lacks connectors.

In the embodiment depicted in FIGS. 10-11A, the medical device 400 includes a first graft portion 410, a second graft portion 420, and a catheter portion 430. The first graft portion 410 and the second graft portion 420 are formed from a single tubular structure 401. In other words, in addition to forming the first graft portion 410 and the second graft portion 420, the single tubular structure 401 extends through and is a component of the catheter portion 430. The remaining component of the catheter portion 430—tubular structure 434—may be analogous or identical in composition and structure to the catheter portions (e.g., catheter portions 130, 230) discussed above.

The inner surface of a lumen 405 formed by the first graft portion 410, the second graft portion 420, and the catheter portion 430 has a smooth continuous surface that extends across the first graft portion 410, the second graft portion 420, and the catheter portion 430. Such a smooth and continuous luminal surface may reduce the extent of blood turbulence and clotting.

FIG. 11B provides a cross-sectional side view of a medical device 400' according to another embodiment. The medical device 400' is generally analogous to the medical device 400 discussed above in connection with FIGS. 10 and 11A. The medical device 400' includes a first graft portion 410', a second graft portion 420', and a catheter portion 430'. In the depicted embodiment, the first graft portion includes 410' includes a portion of a tubular structure 401' that extends through the medical device 400', a portion of a porous PTFE layer 407', and an intervening layer 415'. The second graft portion 420' may likewise include a portion of the tubular structure 401', a portion of a porous PTFE layer 407', and an intervening layer 425'. The catheter portion 430' includes a portion of the tubular structure 401', the tubular structure 434, and a portion of the porous PTFE layer 423'. In some embodiments, the tubular structure 401' is analogous in composition and/or structure to the first graft portions (e.g., first graft portions 110 and 120) discussed above in other embodiments.

In some embodiments, the porous PTFE layer 407' and/or the tubular structure 401' is formed from expanded PTFE. In other embodiments, the porous PTFE layer 407' and/or the tubular structure 401' is formed from fibrous PTFE, such as electrospun or rotational spun PTFE. The porous PTFE layer(s) 407' and/or 401' can reduce thrombus formation and/or promote tissue incorporation (while eliciting little or no inflammation). (In some embodiments, the porous PTFE layer 407' and/or the tubular structure 401' may be replaced with a silicone layer. The silicone may be applied via a spray or could be formed as an extruded tube. The silicone layer may be configured for contact with blood.)

In some embodiments, each of the intervening layers 415' and 425' comprises or consists of fluorinated ethylene propylene (FEP). In other embodiments, no intervening layers are used. For example, in some embodiments, the porous PTFE layer 407' may be thicker adjacent the lateral ends of the medical device 400' than in a medial region of the medical device 400'. In such embodiments, a single porous PTFE layer may occupy the regions identified in FIG. 11B with reference numbers 407',415', and 425'.

In some embodiments, the medical device 400' may have a constant inner diameter (e.g., a diameter defined by the tubular structure 401'. In other or further embodiments, the medical device 400' may have a constant outer diameter (e.g., a diameter defined by the porous PTFE layer 407'. The constant diameter(s) of the inner and/or outer layers may improve biocompatability and reduce thrombus formation of the medical device 400', facilitate placement of the medical device 400', and/or decrease fluid turbulence through the lumen 405' of the medical device 400'.

Figure 12:
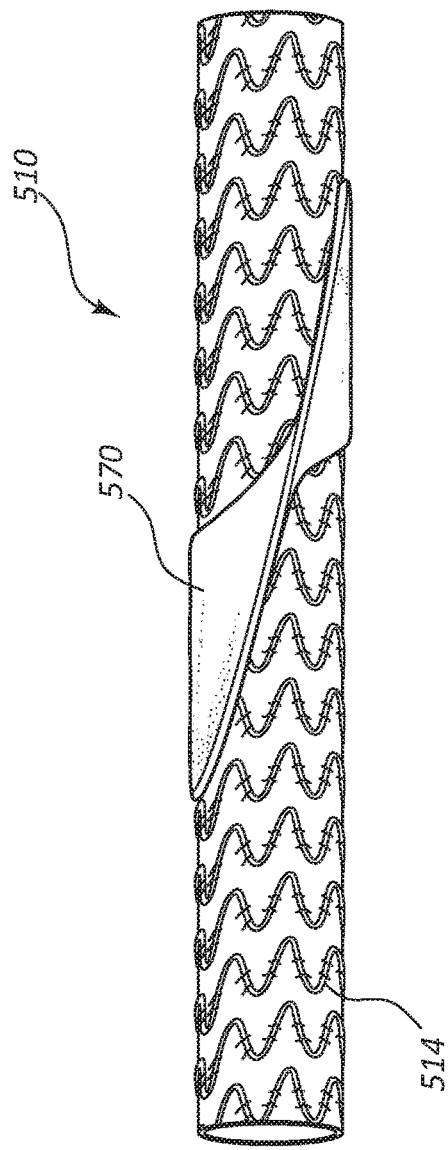
FIG. 12 provides a side view of a portion of a medical device according to another embodiment in which a collapsed collar is disposed around a periphery of a graft portion.
Figure 13:
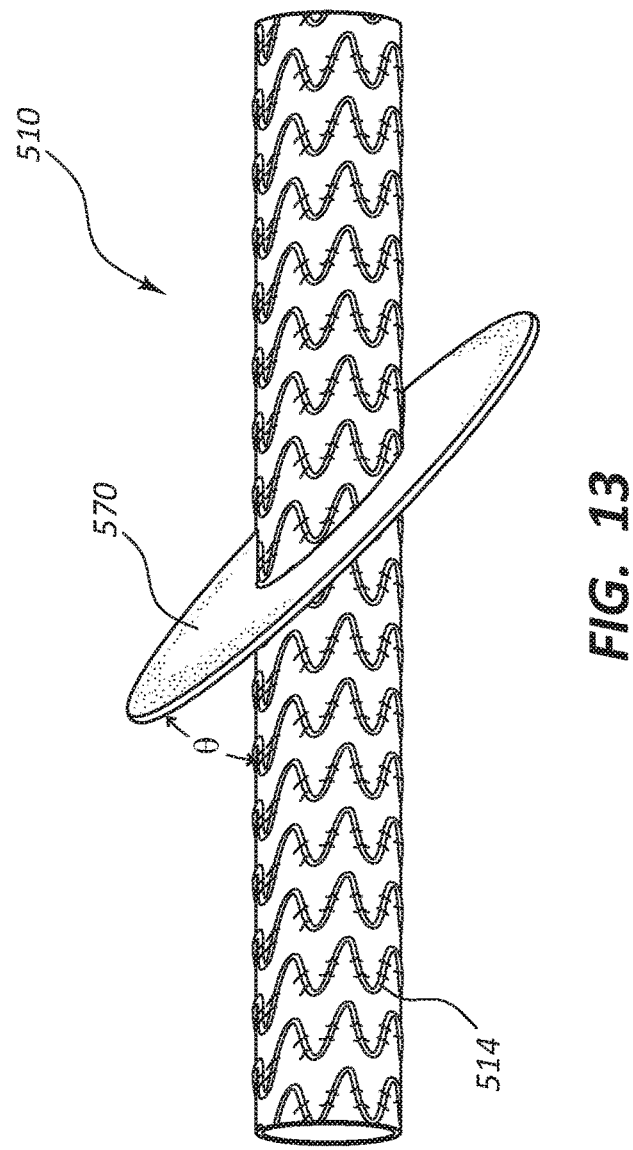
FIG. 13 provides a side view of the portion of the medical device of FIG. 12, with the collar in an uncollapsed configuration.
Figure 14:
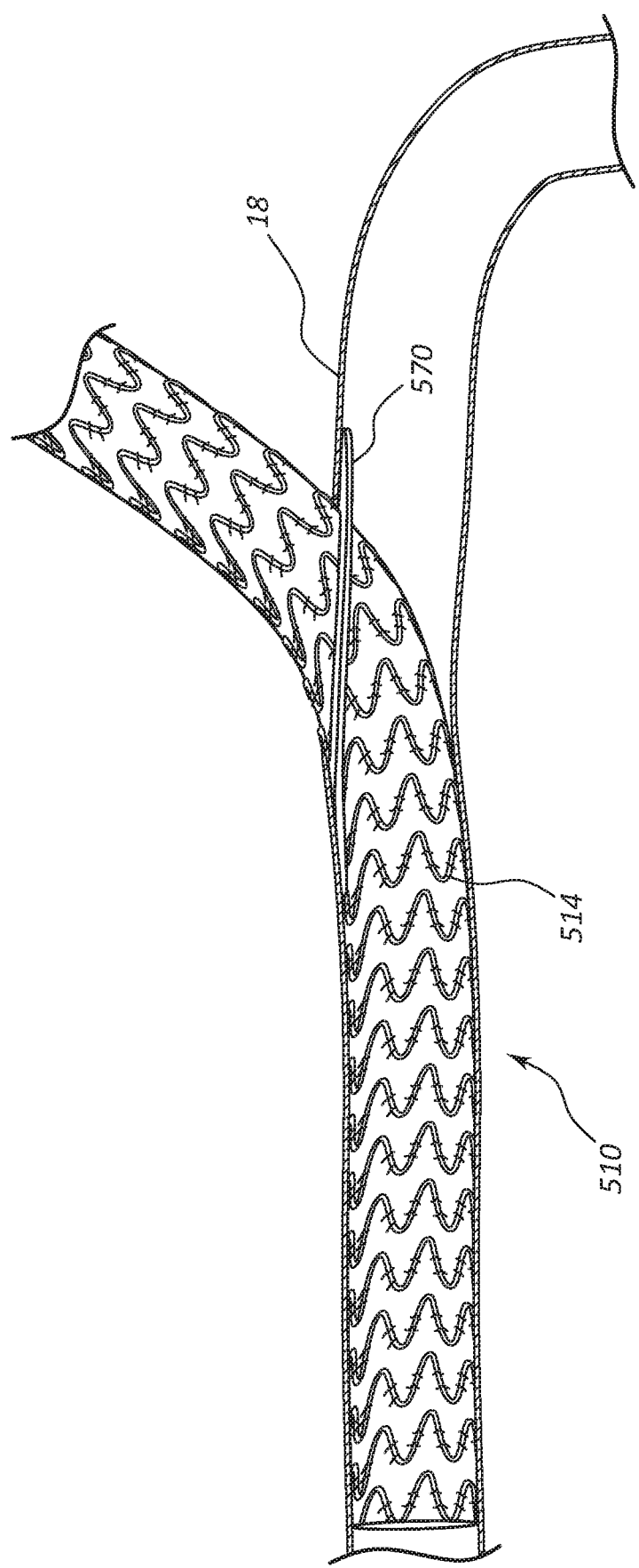
FIG. 14 provides a cross-sectional side view of the portion of the medical device of FIGS. 12 and 13 that is partially disposed within the vasculature of a patient.

FIGS. 12-14 provide distinct configurations of an alternative graft portion 510 for a medical device. The graft portion 510 may be used in a manner analogous to the first graft portions and second graft portions described above. In the depicted embodiment, the graft portion 510 includes a porous tube 514 that extends along substantially the entire length of the graft portion 510. The porous tube 514 may increase the crush force and/or hoop force of the graft portion 510 relative to embodiments that lacks the porous tube 514.

The graft portion 510 may additionally or alternatively include a collar 570 that is disposed around a periphery of the remainder of the graft portion 510. In some embodiments, the collar 570 is configured to transition between a compact state (FIG. 12) in which the collar 570 adopts a low-profile configuration to a deployed state (FIGS. 13 and 14) in which the collar 570 extends outward from the exterior surface of the remainder of the graft portion 510. To attach the graft portion 510 to the vasculature 18 of the patient, the lateral end of the graft portion 510 may initially be inserted into the vasculature 18 (e.g., an artery or vein) of the patient while the collar 570 is in a compact state (e.g., as shown in FIG. 12). Once the graft portion 510 has been partially inserted into the vasculature 18 of the patient, the collar 570 may transition to the deployed state as shown in FIG. 13.

In some embodiments, the porous tube 514 of the graft portion 510 is expandable such that the graft portion 510 is configured to transition from a relatively compact state within a deployment device to an expanded state when deployed through the deployment device. In some instances, the collar 570 may be deployed before the entire graft portion 510 is deployed to facilitate positioning of the graft portion 510. For example, the expanded collar 570 may be brought into contact with a wall of the vasculature 18 of the patient before the entire graft portion 510 is expanded and is thus more easily displaceable. The collar 570 may be any suitable shape. For example, in the depicted embodiment, the collar 570 is a relatively thin, ring-shaped sheet of material.

In some embodiments, the collar 570, when unconstrained, is angled relative to the remainder of the graft portion 510. For example, the collar 570 may form an acute angle (θ) with the remainder of the graft portion 510. In some embodiments, the acute angle θ is between 15° and 75°, between 30° and 60°, and/or between 35° and 55°. The angled relationship between the collar 570 and the remainder of the graft portion 510 may facilitate positioning of the collar 570 to function as a seal. For example, as shown in FIG. 14, the deployed collar 570 may function as a seal, thereby preventing or reducing the leakage of blood from the opening in the vasculature 18 into which the graft portion 510 has been inserted. The collar 570 may also prevent or reduce the risk of withdrawal of the graft portion 510 from the vasculature 18. Stated differently, the collar 570 may serve as a stop that prevents withdrawal of the graft portion 510 from the vasculature 18. In other embodiments, one or more graft portions of the medical device is attached to vasculature via other methods (e.g., traditional anastomosis). In some embodiments, one or more graft portions are attached via sutures. In some embodiments, one or more graft portions are attached via suture-less fasteners, such as staples.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A medical device comprising:
   a catheter portion;
   a first graft portion that is attached to the catheter portion via a first connector comprising a first clamp and a first elongate tube disposed partially in the first graft portion and the catheter portion, wherein the first clamp includes two opposite portions comprising teeth interlocking with one another and is secured over a portion of the first graft portion and the first elongate tube;
   a second graft portion that is attached to the catheter portion via a second connector comprising a second clamp and a second elongate tube disposed partially in the second graft portion and the catheter portion, wherein the second clamp includes two opposite portions comprising teeth interlocking with one another and is secured over a portion of the second graft portion and the second elongate tube; and
   a collar disposed around a periphery between opposing end regions of at least one of the first graft portion and the second graft portion,
   wherein the first graft portion and the second graft portion are fabricated from a flexible material that is suitable for anastomosis to a vein or artery of a patient,
   wherein the catheter portion comprises a porous tube extending from a first end to a second end of the catheter portion,
   wherein the collar comprises a deployed configuration and a compact configuration, wherein, when in the deployed configuration, the collar extends away from the first graft portion or the second graft portion around the entire periphery of the first graft portion or the second graft portion, a first portion of the collar is disposed at an acute angle relative to the first graft portion or the second graft portion in a proximal direction and a second portion of the collar is disposed at an acute angle relative to the first graft portion or the second graft portion in a distal direction, and
   wherein, when in the compact configuration, the first portion of the collar is flat against the first graft portion or the second graft portion in the proximal direction and the second portion of the collar is flat against the first graft portion or the second graft portion in the distal direction.

2. The medical device of claim 1, wherein one or both of the first graft portion and the second graft portion comprises a porous tube.

3. The medical device of claim 2, wherein the porous tube comprises a metal alloy.

4. The medical device claim 2, wherein one or both of the first graft portion and the second graft portion comprises a medial portion and a lateral portion, wherein the medial portion comprises the porous tube and the lateral portion is devoid of the porous tube.

5. The medical device claim 1, wherein the first graft portion and the second graft portion have a lower crush force and a lower hoop force than the catheter portion.

6. The medical device of claim 1, wherein one or both of the first graft portion and the second graft portion comprise porous PTFE.

7. The medical device of claim 1, wherein either or the first graft portion is configured to be attached to a vasculature of a patient at a first location via a first suture-less fastener; or the second graft portion is configured to be attached to the vasculature of the patient at a second location via a second suture-less fastener.

8. The medical device of claim 1, wherein the first connector and the second connector are designed to create a continuous luminal surface that resists thrombus formation.

9. The medical device of claim 1, wherein at least one of the first graft portion, the second graft portion, and the catheter portion comprise a cell impermeable layer.

10. The medical device of claim 9, wherein the entire medical device comprises a cell impermeable layer.

11. A medical device comprising:
    a catheter portion with a first end and second end;
    a first graft portion with a first end and a second end, the second end is attached to the catheter portion via a first connector, wherein the first graft portion includes an inner layer, an outer layer, and an intervening layer disposed between the inner layer and the outer layer, the intervening layer including one or more of fluorinated ethylene propylene, silicone, or polyether block amide; and
    a collar disposed around a periphery between opposing end regions of the first graft portion,
    wherein the second end of the first graft portion comprises a porous tube that comprises a metal alloy disposed in the intervening layer between the inner layer and the outer layer of the first graft portion,
    wherein the first end is fabricated from a flexible material that is suitable for anastomosis to a vein or artery of a patient,
    wherein the catheter portion comprises a porous tube extending from the first end to the second end of the catheter portion,
    wherein the collar comprises a deployed configuration and a compact configuration, wherein, when in the deployed configuration, the collar extends away from the first graft portion around the entire periphery of the first graft portion, a first portion of the collar is disposed at an acute angle relative to the first graft portion in a proximal direction and a second portion of the collar is disposed at an acute angle relative to the first graft portion in a distal direction, and wherein, when in the compact configuration, the first portion of the collar is flat against the first graft portion in the proximal direction and the second portion of the collar is flat against the first graft portion in the distal direction.

12. The medical device of claim 11, further comprising a second graft portion that is attached to the catheter portion via a second connector.

13. A kit comprising:
a catheter;
a first connector that is configured for coupling a first graft to the catheter, the first connector comprising a first clamp and a first elongate tube sized to be disposed partially in the first graft and the catheter portion, wherein the first clamp includes two opposite portions comprising teeth configured to interlock with one another and secure over a portion of the first graft and the first elongate tube;
a second connector that is configured for coupling a second graft to the catheter, the second connector comprising a second clamp and a second elongate tube sized to be disposed partially in the second graft and the catheter portion, wherein the second clamp includes two opposite portions comprising teeth configured to interlock with one another and secure over a portion of the second graft and the second elongate tube;
a collar disposed around a periphery between opposing end regions of at least one of the first graft and the second graft; and
instructions for implanting the catheter, the first graft, and the second graft into a patient such that the first graft is coupled to the catheter via the first connector and the second graft is coupled to the catheter via the second connector,
wherein the first graft and the second graft are fabricated from a flexible material that is suitable for anastomosis to a vein or artery of a patient,
wherein the catheter comprises a porous tube extending from a first end to a second end of the catheter, wherein the collar comprises a deployed configuration and a compact configuration, wherein, when in the deployed configuration, the collar extends away from the first graft or the second graft around the entire periphery of the first graft or the second graft, a first portion of the collar is disposed at an acute angle relative to the first graft or the second graft in a proximal direction and a second portion of the collar is disposed at an acute angle relative to the first graft or the second graft in a distal direction, and wherein, when in the compact configuration, the first portion of the collar is flat against the first graft or the second graft in the proximal direction and the second portion of the collar is flat against the first graft or the second graft in the distal direction.

14. The kit of claim 13, further comprising the first graft and the second graft.

15. The kit of claim 14, further comprising a cutting device configured for shortening one or both of the first graft and the second graft.

16. The kit of claim 14, wherein the instructions specify that the first graft is to be attached to vasculature of a patient at a location that is above the knee of the patient and the second graft is to be attached to vasculature of a patient at a location that is below the knee of the patient.

17. The kit of claim 14, wherein the first graft comprises a porous tube.

18. The kit of claim 14, wherein the catheter has a higher crush force and a higher hoop force than the first graft and the second graft.

19. The kit of claim 14, wherein at least a portion of the first graft, the second graft, or the catheter comprises a cell impermeable layer.

* * * * *